US012735383B2

(12) United States Patent
Johannsen et al.

(10) Patent No.: US 12,735,383 B2
(45) Date of Patent: Sep. 15, 2026

(54) LACTATE/KETONE BODY ESTERS

(71) Applicants: Aarhus Universitet, Aarhus C (DK); Region Midtjylland, Viborg (DK)

(72) Inventors: Mogens Johannsen, Hinnerup (DK); Niels Møller, Aarhus N (DK); Thomas Bjørnskov Poulsen, Højbjerg (DK); Jacob Marthinsen Seefeldt, Aarhus C (DK); Bent Roni Ranghøj Nielsen, Hinnerup (DK); Jakob Hansen, Galten (DK); Rasmus Nørbøge Ottosen, Aarhus C (DK)

(73) Assignees: Aarhus Universitet, Aarhus C (DK); Region Midtjylland, Viborg (DK)

( * ) Notice: Subject to any disclaimer, the term of this patent is extended or adjusted under 35 U.S.C. 154(b) by 572 days.

(21) Appl. No.: 18/251,216

(22) PCT Filed: Nov. 5, 2021

(86) PCT No.: PCT/EP2021/080748

§ 371 (c)(1),
(2) Date: Apr. 28, 2023

(87) PCT Pub. No.: WO2022/096637

PCT Pub. Date: May 12, 2022

(65) Prior Publication Data

US 2023/0399288 A1 Dec. 14, 2023

(30) Foreign Application Priority Data

Nov. 5, 2020 (EP) .................................... 20205938

(51) Int. Cl.
*C07C 69/675* (2006.01)

(52) U.S. Cl.
CPC .................................. *C07C 69/675* (2013.01)

(58) Field of Classification Search
CPC .. C07C 69/675; A61P 1/18; A61P 3/04; A61P 9/00; A61P 9/04; A61P 9/10; A61P 17/02; A61P 25/08; A61P 25/28; A61P 29/00; A61P 31/12; A61P 35/00; A61P 37/00; A61P 43/00; A61K 31/02
USPC .......................................................... 514/546
See application file for complete search history.

(56) References Cited

U.S. PATENT DOCUMENTS

| | | | |
|---|---|---|---|
| 4,675,177 | A | 6/1987 | Geary |
| 8,642,654 | B2 | 2/2014 | Clarke et al. |
| 2011/0237666 | A1 | 9/2011 | Clarke et al. |

FOREIGN PATENT DOCUMENTS

| | | | |
|---|---|---|---|
| WO | WO 2004/105742 A1 | 12/2004 | |
| WO | WO 2004/108740 A2 | 12/2004 | |
| WO | WO 2009/089144 A1 | 7/2009 | |
| WO | WO 2010/021766 A1 | 2/2010 | |
| WO | WO 2012/131069 A1 | 10/2012 | |
| WO | WO 2013/150153 A1 | 10/2013 | |
| WO | WO 2019/125693 A1 | 6/2019 | |

OTHER PUBLICATIONS

Hirakura et al International Journal of Pharmaceutics, 2006, 325, 26-38 (Year: 2006).*
Ichai et al.: "Sodium lactate for fluid resuscitation: the preferred solution for the coming decades?", Critical Care 2014, 18:163.
Duburcq et al.: "Hypertonic sodium lactate improves fluid balance and hemodynamics in porcine endotoxic shock", Critical Care 2014, 18:467.
Nalos et al.: "The comparative effects of 3% saline and 0.5M sodium lactate on cardiac function:a randomised, crossover study in volunteers", Critical Care and Resuscitation, vol. 20, No. 2, Jun. 2018, pp. 124-130.
Gormsen et al.: "Ketone Body Infusion With 3-Hydroxybutyrate Reduces Myocardial Glucose Uptake and Increases Blood Flow in Humans: A Positron Emission Tomography Study", Journal of the American Heart Association, 2017, pp. 1-11.
Koutnik et al.: "Ketone Bodies Attenuate Wasting in Models of Atrophy", Journal of Cachexia, Sarcopenia and Muscle (2020), pp. 1-24.
Rabinowitz et al.: "Lactate: the ugly duckling of energy metabolism", Nature Metabolism, vol. 2, Jul. 2020, pp. 566-571.
Mayer et al.: "Synthesis of New Didemnin B Analogs for Investigations of Structure/Biological Activity Relations", J. Org. Chem., 1994, 59, pp. 5192-5205.
Sun et al.: "Lactic Acid: No Longer an Inert and End-Product of Glycolysis", Physiology, 2017, 32, pp. 453-463.
Puchalska et al.: "Multi-dimensional Roles of Ketone Bodies in Fuel Metabolism, Signaling, and Therapeutics", Cell Metab. 2017 25, pp. 262-284.
Nielsen et al.: "Cardiovascular Effects of Treatment With the Ketone Body 3-Hydroxybutyrate in Chronic Heart Failure Patients", Circulation. 2019, 139, pp. 2129-2141.
Thomsen et al.: "Effects of 3-hydroxybutyrate and free fatty acids on muscle protein kinetics and signaling during LPS-induced inflammation in humans: anticatabolic impact of ketone bodies", Am. J. Clin. Nutr. 2018, 108, pp. 857-867.
Lauritsen et al.: "Ketone Body Infusion Increases Circulating Erythropoietin and Bone Marrow Glucose Uptake", Diabetes Care. 2018, 41, e152-e154.
Petersen et al.: "Mechanisms of Insulin Action and Insulin Resistance". Physiol Rev. 98, 2133-2223 (2018).
Sørensen et al.: Simultaneous determination of β-hydroxybutyrate and β-hydroxy-β-methylbutyrate in human whole blood using hydrophilic interaction liquid chromatography electrospray tandem mass spectrometry, Clinical Biochemistry, vol. 46, Issue 18, 2013, pp. 1877-1883.

(Continued)

*Primary Examiner* — Yevgeny Valenrod
(74) *Attorney, Agent, or Firm* — KNOBBE, MARTENS, OLSON & BEAR, LLP

(57) ABSTRACT

The present invention relates to a Lactate/Ketone body ester for preservation of vital organ function and combat inflammation and cancer growth. In particular, the present invention relates to a Lactate/Ketone body ester with the beneficial properties of Lactate and beta-hydroxybutyrate (BHB) on vital organ function, inflammation and cancer growth but without the harmful sodium loads following administration of both Lactate and beta-hydroxybutyrate.

16 Claims, 6 Drawing Sheets

(56) References Cited

OTHER PUBLICATIONS

Database Registry. Chemical Abstracts Service, Columbus, Ohio, US: Nov. 16, 1984.
Database Registry. Chemical Abstracts Service, Columbus, Ohio, US: Aug. 21, 1985.
Database Registry. Chemical Abstracts Service, Columbus, Ohio, US: Nov. 16, 1984, accession No. 14396-73-7.
Brooks et al: "Lactate in contemporary biology: A phoenix risen", J. Physiol. (2021), pp. 1-23.

* cited by examiner n=8, Sprague Dawley rats. La-Ke dose: 4500mg/kg

A

2way ANOVA, *p<0.05, p<0.01, *p<0.001, ****p<0.0001

2way ANOVA, *p<0.05, p<0.01, *p<0.001, ****p<0.0001

A

2way ANOVA, *p<0.05, p<0.01, *p<0.001, ****p<0.0001

B

2way ANOVA, *p<0.05, p<0.01, *p<0.001, ****p<0.0001

2way ANOVA, *p<0.05, p<0.01, *p<0.001, ****p<0.0001

2way ANOVA, p<0,0001

LACTATE/KETONE BODY ESTERS

CROSS REFERENCE TO RELATEED APPLICATIONS

This application is a U.S. National Phase Application of PCT International Application Number PCT/EP2021/080748, filed on Nov. 5, 2021, designating the United States of America and published in the English language, which is an International Application of and claims the benefit of priority to European Patent Application No. 20205938.2, filed on Nov. 5, 2020. The disclosures of the above-referenced applications are hereby expressly incorporated by reference in their entireties.

TECHNICAL FIELD OF THE INVENTION

The present invention relates to Lactate/Ketone body esters (LaKe) for preservation of vital organ function and combat inflammation, cancer growth, sarcopenia and atherosclerosis. In particular, the present invention relates to Lactate/Ketone body esters with the beneficial properties of lactate or lactate and ketone bodies such as beta-hydroxybutyrate (BHB) on vital organ function, inflammation and cancer growth but without harmful ion loads, such as calcium potassium, magnesium and/or sodium loads following administration of both Lactate and beta-hydroxybutyrate salts.

BACKGROUND OF THE INVENTION

Lactate ($C_3H_6O_3$) and ketone bodies, notably beta-hydroxybutyrate (BHB—$C_4H_8O_3$), are low molecular weight carbon fuel metabolites with many similarities: both are highly $O_2$ efficient agents produced and used by the human body as an energy source (1,2,8). They have protective properties during stress and act through similar, yet distinct, tissue receptors (1,2). Lactate and ketone bodies contribute to the health-promoting effects of exercise, intermittent fasting, a ketogenic diet, and SGLT-2 inhibition in diabetes. In addition, preclinical studies strongly suggest that both compounds (alone or in combination) effectively counteract inflammation, cancer growth, protein loss and neurodegeneration (1, 2). We have recently found striking beneficial clinical effects of BHB in the heart, brain, skeletal muscle and bone marrow (increased Epo) in terms of increased blood flow and improved organ function (3-5). The possible beneficial effects of lactate are currently being investigated in human studies and Ringers lactate (Sodium lactate) is used routinely in the emergency room. Several pre-clinical studies suggest multiple beneficial effects of lactate (1,2,6-9).

WO04/105742 teaches that compounds which reduce the level of free fatty acids circulating in the plasma of a subject may be used e.g. to treat muscle impairment or fatigue.

US 2011/0237666 A1 discloses 3-hydroxybutyl 3-hydroxybutyrate enantiomerically enriched with respect to (3R)-hydroxybutyl (3R)-hydroxybutyrate, as oral precursor of (3R)-hydroxybutyrate, for use in the treatment of a condition which is caused by, exacerbated by or associated with elevated plasma levels of free fatty acids in a human or animal subject; cognitive dysfunction, neurodegenerative diseases, for instance Alzheimer's disease, Parkinson's disease, Huntington's chorea, epilepsy; hypoxic states, for instance angina pectoris, extreme physical exertion, intermittent claudication, hypoxia, stroke and myocardial infarction; insulin resistant states, for instance infection, stress, obesity, diabetes, metabolic syndrome and heart failure; inflammatory states including infection and autoimmune disease and muscle impairment, fatigue and muscle fatigue. It is further disclosed that the compound reduces plasma levels of fatty acids and may be used for e.g. treating a condition which is caused by, exacerbated by or associated with elevated plasma levels of free fatty acids in a human or animal subject.

WO 2012/131069 A1 describes short chain fatty acid derivatives such as propyl 3-hydroxypropionate and propyl propionate for use in the treatment of immunogenic disorders such as inflammatory diseases and viral infection (e.g. hepatitis).

DATABASE REGISTRY [Online] CHEMICAL ABSTRACTS SERVICE; 16 Nov. 1984, accession no. 14451-61-7 (Database accession no. 14451-61-7) describes 3-Hydroxypropyl butanoate.

DATABASE REGISTRY [Online] CHEMICAL ABSTRACTS SERVICE; 21 Aug. 1985, accession no. 93981-64-7 (Database accession no. 93981-64-7) describes 3-Hydroxybutyl 2-hydroxypropanoate.

DATABASE REGISTRY [Online] CHEMICAL ABSTRACTS SERVICE; 16 Nov. 1984, accession no. 14396-73-7 (Database accession no. 14396-73-7) describes 2- Hydroxypropyl 2-hydroxypropa noate.

PUCHALSKA PATRYCJA ET AL. ("Multi-dimensional Roles of Ketone Bodies in Fuel Metabolism, Signaling, and Therapeutics", CELL METABOLISM, vol. 25, no. 2, 7 Feb. 2017, pages 262-284) describes the multiple therapeutic implications of ketone bodies in e.g. inflammation and injury in multiple organ systems, heart failure, atherosclerosis, myocardial infarction, cancer, obesity, diabetes, NAFLD/NASH, diseases of the nervous system, oxidative stress.

There is, however, a compelling—and currently unmet—need for suitable preparations of lactate and ketone bodies such as BHB to avoid excessive ion loading such as sodium loading—and a horrible taste. These factors severely limit the amount of both of the metabolites that can be ingested, both with respect to scenarios involving daily ingestion as a food supplement and use in medicinally relevant settings.

Hence, a compound or a method for administration of such a compound to achieve the beneficial properties of lactate and BHB, while minimizing the harmful and unpleasant side effects would be of great importance.

SUMMARY OF THE INVENTION

The present invention relates to the identification of compounds, which can release lactate or lactate and BHB in vivo, called lactate/ketone body esters. Thus, the compounds of the invention can be considered to be prodrugs.

The lactate/ketone body esters will have dual functions limiting e.g. inflammation of general relevance for treating or ameliorating aging-related diseases as well as they are high-energy metabolic substrates. The latter effect is both of relevance for medical use e.g. for improving muscle function or output and/or limiting muscle wasting in hospitalized patients or in the general aging-population. In addition the esters may be relevant as food or nutritional supplements in e.g. endurance or high-performance sports. The esters moreover have a range of further medical uses.

Thus, an object of the present invention relates to providing a compound with the beneficial properties of lactate and BHB.

In particular, it is an object of the present invention to provide a compound, which solves the above-mentioned problems, without compromising the beneficial effects.

In the present context, unless otherwise specified the term “LaKe” refers to compounds with the overall structure:

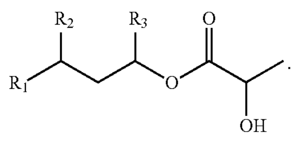

In the present context, unless otherwise specified the term “DiLa” refers to compounds with the overall structure:

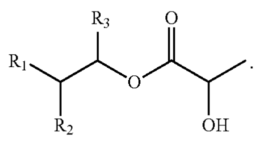

In the present context, unless otherwise specified the term “KeLa” refers to compounds with the overall structure:

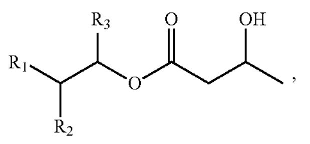

Examples 1-2 show chemical synthesis of LaKe compounds X, XI, XII, and XIII

Example 3 shows chemical synthesis of DiLa compounds XIV and XV.

Example 5 shows that administration of LaKe (structure X and XI), compared to a control, gives rise to an increased serum concentration of both BHB and lactate in rats following oral administration.

Example 6 shows that oral administration of LaKe (structure X and XI) leads to a decreased concentration of FFA in rat serum compared to the control.

Example 7 shows that administration with KeLa (structure XXVI and XXVII), compared to a control, gives rise to an increased serum concentration of both BHB and lactate in rats following oral administration.

Example 8 shows that administration with DiLa (structure XIV and XV), compared to a control, gives rise to an increased serum concentration of lactate in rats following oral administration.

Example 9 shows that oral administration of KeLa (structure XXVI and XXVII), leads to a decreased concentration of FFA in rat serum compared to the control.

Example 10 shows that oral administration of DiLa (structure XIV and XV), does not lead to a decreased concentration of FFA in rat serum compared to the control.

Example 11-12 show Chemoenzymatic synthesis of LaKe and DiLa esters.

Example 13 shows synthesis of R-(−)-3-hydroxybutyric acid esters (KeLa esters) (structure XXVI and XXVII).

Thus, one aspect of the invention relates to a compound of the formula I (I)

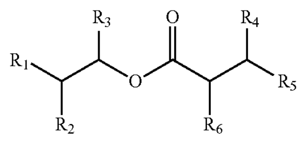

or a pharmaceutical acceptable salt thereof, wherein Ri is H, $CH_3$, OH, $CH_2OH$ or $CH(CH_3)OH$, $R_2$ is H or OH, $R_3$ is H or $CH_3$, $R_4$ and $R_5$ are H, OH or $CH_3$, and $R_6$ is H or OH.

Another aspect of the invention relates to a compound of the formula XXVIII (LaKe)

(XXVIII)

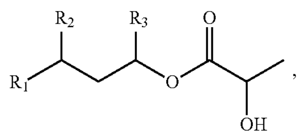

or a compound of the formula II (KeLa I/II)

(XXIX)

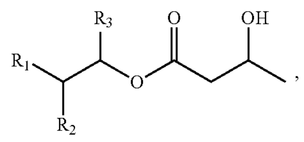

or a compound of formula XXX (DiLa I/II)

(XXX)

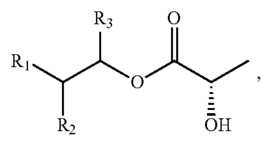

or a pharmaceutical acceptable salt thereof, wherein $R_1$, $R_2$ and $R_3$ are $CH_3$, OH and H respectively or $R_1$, $R_2$ and $R_3$ are OH, H and $CH_3$ respectively.

A further object of the present invention is to provide a compound that can be administered orally.

Thus, another aspect of the present invention is to provide a pharmaceutical composition comprising one or more of the compounds of the present invention.

Figure 1:
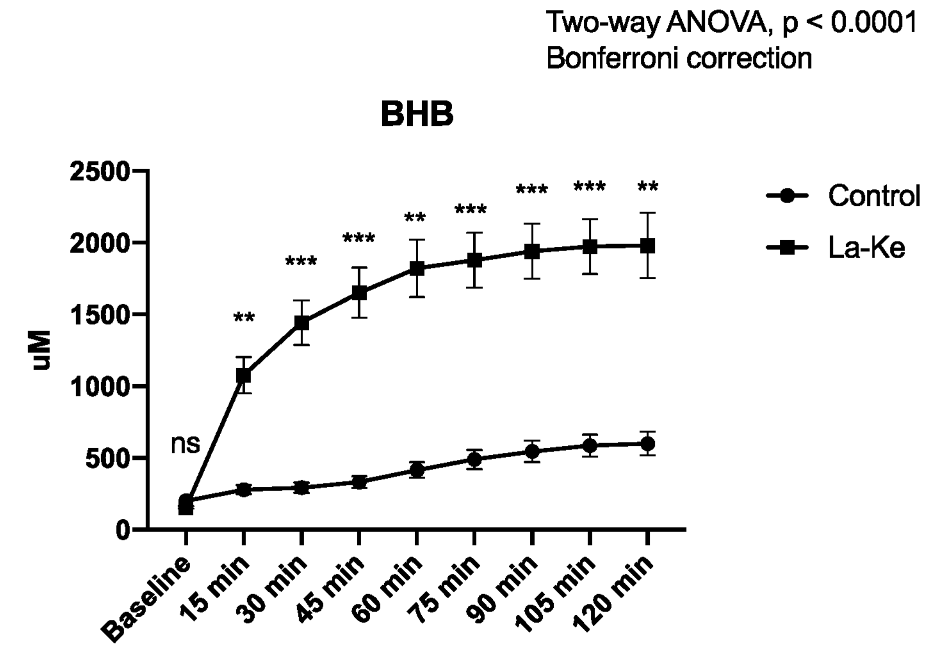
FIG. 1 shows the concentration (μM) of BHB (FIG. 1A) and lactate (FIG. 1B) in rat serum over time, following oral administration of either compound X and XI (LaKe) or physiological saline solution (0.9% NaCl) as a control to rats.
Figure 1:
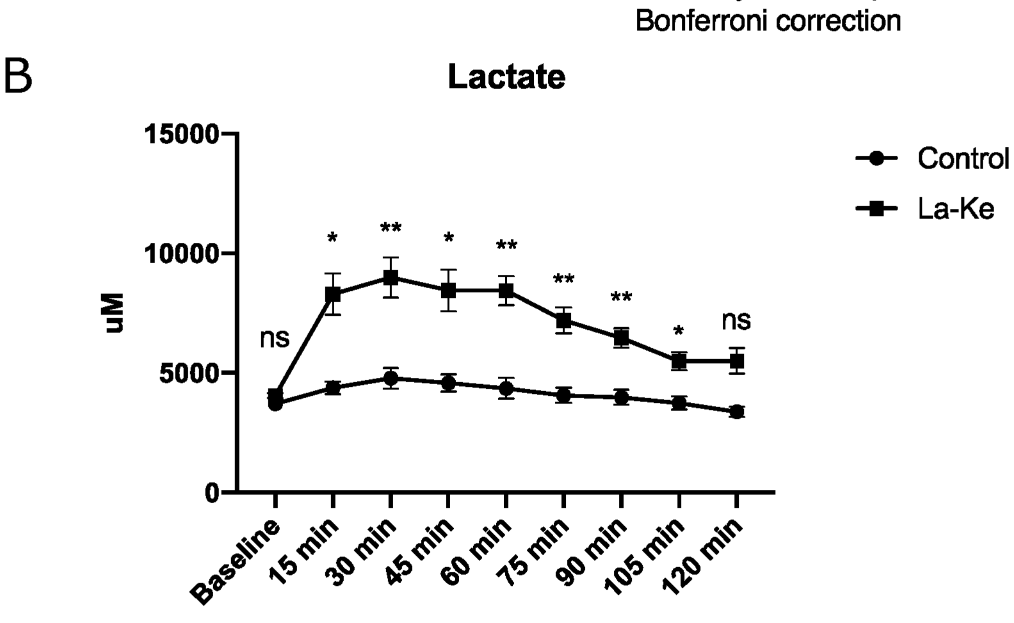

The present invention will now be described in more detail in the following.

DETAILED DESCRIPTION OF THE INVENTION

Definitions

Prior to discussing the present invention in further details, the following terms and conventions will first be defined:

Ketone Body

In the present context the term "ketone body" refers to a water-soluble molecule containing a ketone group or the specific compounds BHB, acetoacetate and acetone. The compound is produced by the liver from fatty acids.

Non-Esterified Free Fatty Acids (FFA)

In the present context, the term "Non-esterified free fatty acid" refers to metabolic fuel e.g. organic acids derived from hydrolysis of endogenous triglycerides. Increased levels of free fatty acids is associated with increased risk of disease.

Oral Administration

In the present context, the term "Oral administration" refers to a route of administration, where the substance is administered through the mouth of the subject.

Subject

The term "subject" comprises humans of all ages, other primates (e.g., cynomolgus monkeys, rhesus monkeys); mammals in general, including commercially relevant mammals, such as cattle, pigs, horses, sheep, goats, mink, ferrets, hamsers, cats and dogs, as well as birds. Preferred subjects are humans.

The term "subject" also includes healthy subjects of the population.

Food

In the present context the term "food" or "food ingredient" is to be understood as also covering "feed" and "feed ingredient". Thus, the food according to the invention may refer both to food/feed suitable for human and/or animal consumption and the term food ingredient according to the invention may refer both to food/feed suitable for human and/or animal consumption.

Generally speaking, the term "feed" refers to animal consumption and the term "food" refers to human or animal consumption. In the broad sense of the invention the terms may be used interchangeably.

Nutraceutical

In the present context, the term "nutraceutical" or "bioceutical" L is to be understood as any substance that is a food or part of a food and may provide medical or health benefits, including the prevention and treatment of disease.

A nutraceutical or 'bioceutical' is a pharmaceutical alternative which claims physiological benefits. In the US, "nutraceuticals" are largely unregulated, as they exist in the same category as dietary supplements and food additives by the FDA, under the authority of the Federal Food, Drug, and Cosmetic Act.

In a preferred embodiment of the present invention, the compound or composition according to the invention, is a nutraceutical or is part of a nutraceutical.

In another preferred embodiment of the present invention, the compound or composition according to the invention, is a pharmaceutical or part of a pharmaceutical.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

Lactate/Ketone Body Esters

The present invention provides a novel group of Lactate/Ketone body esters and synthesis thereof for oral use in animals and humans. The compounds provide the beneficial properties known from lactate and BHB, while preventing the toxic ion load associated with the use of the individual compounds.

Thus, a first aspect of the present invention relates to a compound of the formula I.

(I)

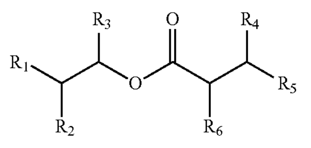

or a pharmaceutical acceptable salt thereof, wherein Ri is H, $CH_3$, OH, $CH_2OH$ or $CH(CH_3)OH$, $R_2$ is H or OH, $R_3$ is H or $CH_3$, $R_4$ and $R_5$ are H, OH or $CH_3$ and $R_6$ is H or OH.

In an embodiment, $R_1$ is $CH(CH_3)OH$, $R_4$ and $R_5$ are H, and $R_6$ is OH.

In yet an embodiment, $R_1$ is $CH(CH_3)OH$, $R_4$ and $R_5$ are H, $R_6$ is OH, and $R_2$ is H.

In an embodiment of the present invention, $R_1$ is $CH(CH_3)OH$.

In another embodiment of the present invention, $R_2$ is H.

In yet another embodiment of the present invention, $R_3$ is H.

In an embodiment, $R_1$ is $CH_2OH$, $R_4$ and $R_5$ are H, and $R_6$ is OH.

In yet an embodiment, $R_1$ is $CH_2OH$, $R_4$ and $R_5$ are H, $R_6$ is OH, and $R_2$ is H.

In a further embodiment of the present invention, $R_4$ is H.

In yet a further embodiment of the present invention, $R_5$ is H.

In an even further embodiment of the present invention, $R_6$ is OH.

In a preferred embodiment of the present invention, $R_1$ is $CH(CH_3)OH$, $R_2$ is H, $R_3$ is H, $R_4$ and $R_5$ are H, and $R_6$ is OH.

As illustrated in formula XXXI, (XXXI)

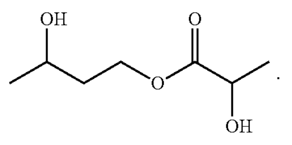

In another embodiment, $R_1$ is $CH_2OH$.

In a further embodiment, $R_3$ is $CH_3$.

In a preferred embodiment, $R_1$ is $CH_2OH$, $R_2$ is H, $R_3$ is $CH_3$, $R_4$ and $R_5$ are H and $R_6$ is OH.

As illustrated in formula XXXII, (XXXII)

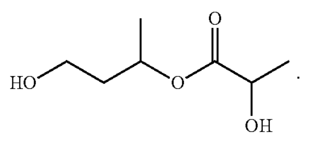

In another embodiment, $R_1$ is $CH_3$.

In yet another embodiment, $R_2$ is OH.

In a preferred embodiment, $R_1$ is $CH_3$, $R_2$ is OH, $R_3$ is H, $R_4$ and $R_5$ are H, and $R_6$ is OH.

In another embodiment, $R_1$ is OH.

In a preferred embodiment, $R_1$ is OH, $R_2$ is H, $R_3$ is $CH_3$, $R_4$ and $R_5$ are H, and $R_6$ is OH.

In an embodiment of the present invention, $R_4$ is $CH_3$.

In another embodiment of the present invention, $R_4$ is OH.

In a further embodiment of the present invention, $R_5$ is $CH_3$.

In yet a further embodiment of the present invention, $R_5$ is OH.

In an even further embodiment of the present invention, $R_6$ is H.

In another preferred embodiment of the present invention, $R_1$ is OH, $R_2$ is H, $R_3$ is $CH_3$, $R_4$ is OH, $R_5$ is $CH_3$, and $R_6$ is H, as illustrated in formula XXXIV, (XXXIV)

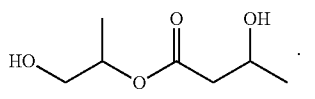

In a further preferred embodiment of the present invention, $R_1$ is $CH_3$, $R_2$ is OH, $R_3$ is H, $R_4$ is OH, $R_5$ is $CH_3$, and $R_6$ is H, as illustrated in formula XXXIII, (XXXIII)

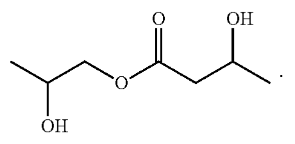

The compound of formula I can contain different asymmetric C atoms and can therefore be presented in different isoforms.

One embodiment of the present invention relates to a compound of formula II, (II)

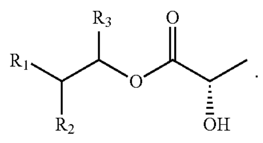

In another preferred embodiment of the present invention, $R_1$ is $CH_3$, $R_2$ is OH, $R_3$ is H, $R_4$ is H, $R_5$ is H, and $R_6$ is OH. As illustrated in formula XXXV with the stereochemistry according to formula II, (XXXV)

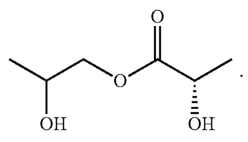

In a preferred embodiment of the present invention, $R_1$ is OH, $R_2$ is H, $R_3$ is $CH_3$, $R_4$ is H, $R_5$ is H, and $R_6$ is OH. As illustrated in formula XXXVI with the stereochemistry according to formula II, (XXXVI)

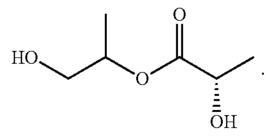

Another embodiment of the present invention relates to a compound of formula III, (III)

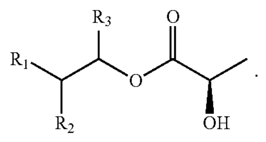

Another embodiment of the present invention related to a compound of formula IV, wherein $R_1$ and $R_2$ are different and not H, (IV)

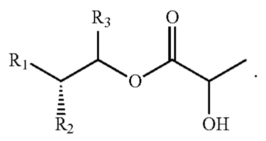

Another embodiment of the present invention relates to a compound of formula V, $R_1$ and $R_2$ are different and not H, (V)

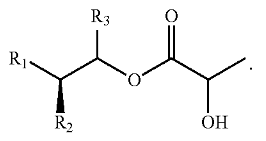

Another embodiment of the present invention related to a compound of formula VI, wherein $R_3$ is $CH_3$, (VI)

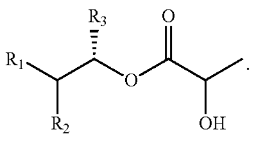

Another embodiment of the present invention relates to a compound of formula VII, wherein $R_3$ is $CH_3$, (VII)

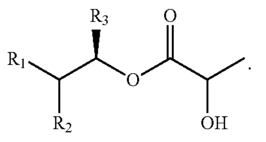

Another embodiment of the present invention related to a compound of formula VIII, (VIII)

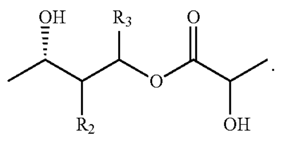

Another embodiment of the present invention relates to a compound of formula IX, (IX)

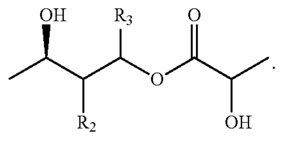

Another aspect of the present invention relates to a compound of the formula XXVIII (LaKe I/II)

(XXVIII)

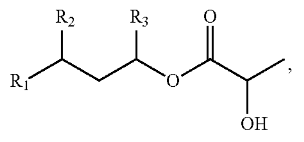

or a compound of the formula II (KeLa I/II)

(XXIX)

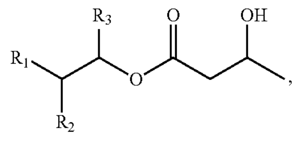

or a compound of formula XXX (DiLa I/II)

(XXX)

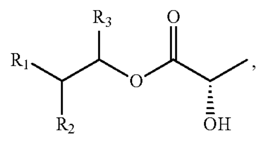

or a pharmaceutical acceptable salt thereof, wherein $R_1$ is $CH_3$ or OH, $R_2$ is OH or H and $R_3$ is $CH_3$ or H.

A further aspect of the present invention relates to a compound of the formula XXVIII (LaKe I/II)

(XXVIII)

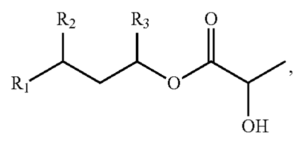

or a compound of the formula II (KeLa I/II)

(XXIX)

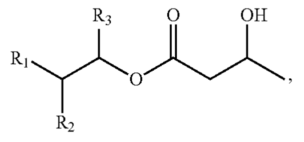

or a compound of formula XXX (DiLa I/II)

(XXX)

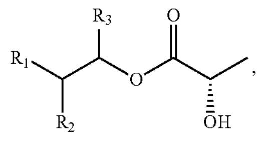

or a pharmaceutical acceptable salt thereof, wherein $R_1$, $R_2$ and $R_3$ are $CH_3$, OH and H respectively or Ri, $R_2$ and $R_3$ are OH, H and $CH_3$ respectively.

Structure XXVIII, XXIX and XXX have been tested in examples 4-10.

The compounds of formula XXVIII, XXIX and XXX can contain different asymmetric C atoms and can therefore be presented in different isoforms.

Thus, in one embodiment, the present invention relates to a compound of formula XXXVII, (XXXVII)

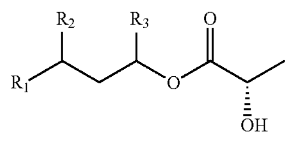

or a pharmaceutical acceptable salt thereof.

In another embodiment, the present invention relates to a compound of formula XXXVIII, (XXXVIII)

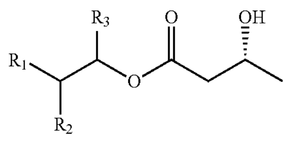

or a pharmaceutical acceptable salt thereof.

In a further embodiment, the present invention relates to a compound of formula XXXIX, (XXXIX)

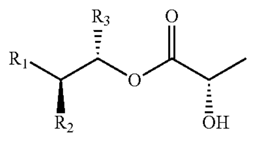

or a pharmaceutical acceptable salt thereof.

In a preferred embodiment, the present invention relates to a compound of formula X, (X)

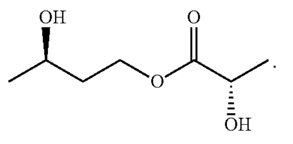

In another preferred embodiment, the present invention relates to a compound of formula XI, (XI)

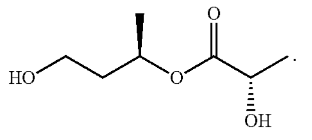

Structure X and XI have been tested in examples 4-6.

In another preferred embodiment, the present invention relates to a compound of formula XII, (XII)

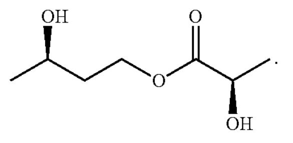

In another preferred embodiment, the present invention relates to a compound of formula XIII, (XIII)

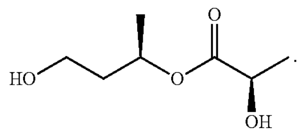

In another preferred embodiment, the present invention relates to a compound of formula XIV, (XIV)

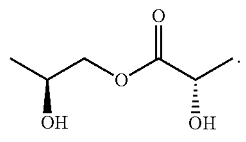

In another preferred embodiment, the present invention relates to a compound of formula XV, (XV)

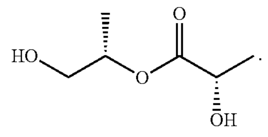

Structure XIV and XV have been tested in examples 8 and 10.

In another preferred embodiment, the present invention relates to a compound of formula XVI, (XVI)

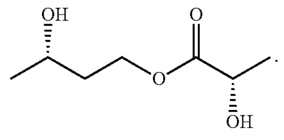

In another preferred embodiment, the present invention relates to a compound of formula XVII, (XVII)

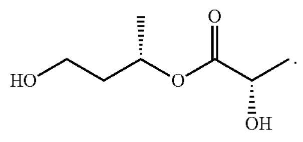

In another preferred embodiment, the present invention relates to a compound of formula XVIII (XVIII)

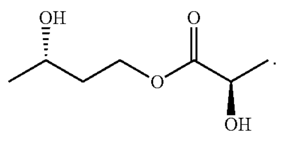

In another preferred embodiment, the present invention relates to a compound of formula XIX, (XIX)

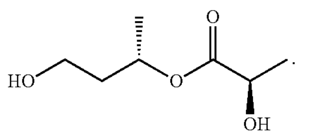

In another preferred embodiment, the present invention relates to a compound of formula XX, (XX)

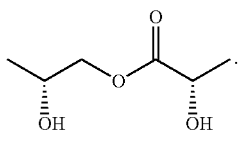

In another preferred embodiment, the present invention relates to a compound of formula XXI, (XXI)

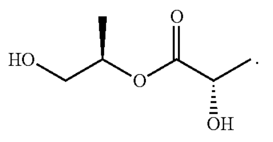

In another preferred embodiment, the present invention relates to a compound of formula XXII, (XXII)

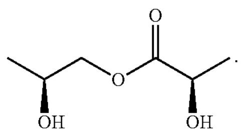

In another preferred embodiment, the present invention relates to a compound of formula XXIII, (XXIII)

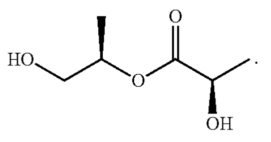

In another preferred embodiment, the present invention relates to a compound of formula XXIV, (XXIV)

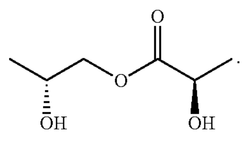

In another preferred embodiment, the present invention relates to a compound of formula XXV, (XXV)

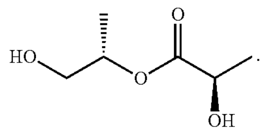

In another preferred embodiment, the present invention relates to a compound of formula XXVI, (XXVI)

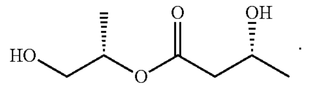

In another preferred embodiment, the present invention relates to a compound of formula XXVII, (XXVII)

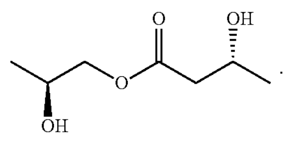

Structure XXVI and XXVII have been tested in examples 7 and 9.

Composition

The compounds according to the present invention can be used in a composition comprising different amounts of the described compounds.

Thus, one aspect of the present invention relates to a composition comprising the compound according to the present invention.

In one embodiment, the present invention relates to a composition comprising a compound according to formula X and a compound according to formula XI, such as in a ratio of formula X to formula XI in the range 100:1 to 1:100, such as in the ratio 50:1 to 1:50, such as in the ratio 25:1 to 1:25, such as in the ratio 25:1 to 1:1, or such as in the range 100:1 to 1:1, such as in the ratio 50:1 to 1:1, or preferably in the ratio 25:1 to 1:1, more preferably in the ratio 25:1 to 5:1.

In another embodiment, the present invention relates to a composition comprising a compound according to formula XXVII and a compound according to formula XXVI, such as in a ratio of formula XXVII to formula XXVI in the range 100:1 to 1:100, such as in the ratio 50:1 to 1:50, such as in the ratio 25:1 to 1:25, or such as in the range 100:1 to 1:1, such as in the ratio 50:1 to 1:1, such as in the ratio to 5:1, preferably in the ratio 25:1 to 1:1, more preferably in the ratio 25:1 to 5:1.

In a further embodiment, the present invention relates to a composition comprising a compound according to formula XIV and a compound according to formula XV, such as in a ratio of formula XIV to formula XV in the range 100:1 to 1:100, such as in the ratio 50:1 to 1:50, such as in the ratio 25:1 to 1:25, or such as in the range 100:1 to 1:1, such as in the ratio 50:1 to 1:1, such as in the ratio 25:1 to 5:1, preferably in the ratio 25:1 to 1:1, more preferably in the ratio 25:1 to 5:1.

In one embodiment, the present invention relates to a composition comprising a compound according to formula XII and a compound according to formula XIII, such as in a ratio of formula XII to formula XIII in the range 100:1 to 1:100, such as in the ratio 50:1 to 1:50, such as in the ratio 25:1 to 1:25, such as in the range 100:1 to 1:1, such as in the ratio 50:1 to 1:1, such as in the ratio 25:1 to preferably in the ratio 25:1 to 1:1, more preferably in the ratio 25:1 to 5:1.

In addition to the compound disclosed in relation to the present invention, the composition may further comprise other ketone esters or ketonebody precursors.

Thus, in one embodiment of the present invention, the composition further comprises one or more ketone esters or ketonebody precursors different from a compound according to any of formula I to XXXIX.

In another embodiment of the present invention, the one or more ketone ester or ketonebody precursors different from a compound according to any of formula I to XXXIX, is selected from the group consisting of 1,3-butanediol diacetoacetate, 1,3-butanediol dihexanoate, 1,3-butanediol, medium chain triglycerides, 3-hydroxybutyl 3-hydroxybutyrate and (3R)-hydroxybutyl (3R)-hydroxybutyrate.

In a further embodiment, the composition according to the invention, further comprises a dietetically and/or pharmaceutically acceptable carrier.

In yet another embodiment, the composition according to the invention, further comprising a sugar carbohydrate.

In yet a further embodiment, the composition according to the invention comprises a combination of one or more compounds selected from the group consisting of formula X, XI, XII, XIII, XIV, XV, XXVI, and XXVII.

Uses

BHB and lactate have been shown to ameliorate or be useful as treatment for a number of different diseases. This both due to their antiinflammatory effects etc., as well as their general effect as high-energy substrates. Furthermore, they will be relevant in relation to endurance or sports performance e.g. via improvement of muscle output/motor function.

Thus an aspect of the present invention relates to a pharmaceudical composition comprising the compounds according to the present invention or the composition according to the present invention.

Thus, in one embodiment the present invention can be used as a medicament.

BHB and lactate have been associated with beneficial outcome when used in the treatment of inflammatory disease, cancer, epileptic seizures, acute heart failure, Resuscitation, acidosis, traumatic brain injury, acute pancreatitis, hepatitis, myocardial infarction, burns, sepsis, dengue, cognition, sarcopenia, atherosclerosis, neurodegeneration, oxidative stress and wound healing.

The compounds of the present invention are able to increase circulating levels of ketone body BHB and/ or lactate (see examples 5, 7 and 8).

Thus, in one embodiment of the present invention the compounds can be used in the treatment, prevention or alleviation of diseases or conditions selected from the group comprising: inflammatory disease, cancer, epileptic seizures, acute heart failure, Resuscitation, acidosis, traumatic brain injury, acute pancreatitis, hepatitis, myocardial infarction, burns, sepsis, dengue, cognition, sarcopenia, atherosclerosis, neurodegeneration, oxidative stress, Alzheimer's disease, Parkinson's disease, amyotrophic lateral sclerosis, epilepsy, astrocytoma, glioblastoma and Huntington's chorea, sarcopenia, muscle atrophy and wound healing.

In yet an embodiment, of the present invention the compounds can be used in the treatment, prevention or alleviation of elevated plasma levels of free fatty acids in a human or animal subject; cognitive dysfunction, neurodegenerative diseases, for instance Alzheimer's disease, Parkinson's disease, Huntington's chorea, epilepsy; hypoxic states, for instance angina pectoris, extreme physical exertion, intermittent claudication, hypoxia, stroke and myocardial infarction; insulin resistant states, for instance infection, stress, obesity, diabetes, metabolic syndrome and heart failure; inflammatory states including infection and autoimmune disease and muscle impairment, fatigue and muscle fatigue. It is further disclosed that the compound reduces plasma levels of fatty acids and may be used for e.g. treating a condition which is caused by, exacerbated by or associated with elevated plasma levels of free fatty acids in a human or animal subject.

The compounds of the present invention are able to lower the level of free fatty acids (FFA) in blood (see examples 6 and 9).

The level of FFA in blood reflects ongoing lipolysis and high levels of FFA induce insulin resistance; conversely agents that lower the level of free fatty acids in the blood can be used therapeutically to increase insulin sensitivity in people with type 2 diabetes and the metabolic syndrome (6).

Thus, in one embodiment of the present invention, the compounds, composition or pharmaceutical composition according to the invention can be used in the treatment, prevention or alleviation of a condition which is caused by, exacerbated by or associated with elevated plasma levels of free fatty acids in a human or animal subject.

The method comprises administering to the subject a compound or composition according to the invention.

Thus, in a preferred embodiment of the present invention, the compounds can be used to control the level of free fatty acids in the blood of the subject.

In another embodiment of the present invention, the compounds can be use in the treatment, prevention or alleviation of viral infections, immunogenic disorders, non-alcoholic fatty liver disease (NAFLD), non-alcoholic steatohepatitis (NASH), sarcopenia, muscle fatigue, angina pectoris, extreme physical exertion, intermittent claudication, hypoxia, stroke and myocardial infarction, stress, obesity, diabetes, metabolic syndrome, autoimmune disease, muscle impairment or to improve motor function.

In one embodiment, the compounds, composition or pharmaceutical composition according to the invention can be used use in the treatment, prevention and/or alleviation of insulin resistance.

In another embodiment, the compound of the present invention can be used in the treatment of insulin resistance, preferably the compound can be used in increasing the insulin sensitivity in the subject.

In yet another embodiment, the compounds of the present invention can be used in a treatment to inhibit or alleviate inflammation, atherosclerosis, neurodegeneration, oxidative stress, carcinogenesis and angiogenesis.

Administration of the compound can be done in a number of ways as described in the following, non-limiting examples. Oral or Nasal, which is administration through the mouth or nose. By intradermal injection, which is a delivery of the compound into the dermis of the skin, located between epidermis and the hypodermis. Alternatively, the compound can be administered intraveneous, which is an administration directly into the blood stream of the subject. Further, intramuscular administration of the compound is an injection into the muscles of the subject. In addition, the compound can be administered subcutaneous, which is under the skin, in the area between the muscle and the skin of the subject. Further, the compound can be administered intratracheal, which is administration directly into the trachea and by transdermal administration, which is administration across the skin.

Any mode of administration can be used as long as the mode results in the desired effect of the compound.

Thus, in one embodiment, the compound is administered to the subject by oral or nasal administration.

In a preferred embodiment, the compound is administered to a subject by oral administration.

In another preferred embodiment, the compounds, composition or pharmaceutical composition according to the invention is orally administered.

The compound as described herein may be administered in doses suitable for providing the desired effect in the subject receiving the compound.

In one embodiment the compound is administered in a dose of 0.05-1.5 g/kg, preferably 0.15-1.5 g/kg, more preferably 0.2-1.0 g/kg, even more preferably 0.2-0.5 g/kg.

In another embodiment the compound, composition or pharmaceutical composition according to the invention is administered in a dose of 0.05-15 g/kg, preferably 0.15-10 g/kg, more preferably 0.2-5 g/kg, even more preferably 0.2-2.5 g/kg, even more preferably 0.2-1.5 g/kg.

In another embodiment the compound, composition or pharmaceutical composition according to the invention is administered in a daily dosage in the range 0.15-45g/kg, preferably 0.45-30 g/kg, more preferably 0.6-15 g/kg or 0.6-4.5 g/Kg, even more preferably 0.6-1.5 g/kg.

The "subject" as described herein is supposed to receive the compound and comprises humans of all ages, other primates (e.g., cynomolgus monkeys, rhesus monkeys); mammals in general, including commercially relevant mammals, such as cattle, pigs, horses, sheep, goats, mink, ferrets, hamsters, cats, dogs; and/or birds in need of the described compounds. Preferred subjects are humans.

The term "subject" also includes healthy subjects of the population.

Thus, in an embodiment of the present invention, the subject is selected from the group consisting of; humans of all ages, other primates (e.g., cynomolgus monkeys, rhesus monkeys); mammals in general, including commercially relevant mammals, such as cattle, pigs, horses, sheep, goats, mink, ferrets, hamsters, cats and dogs, as well as birds.

In a preferred embodiment, the subject is a human.

In one embodiment, the subject being an elderly subject, such as a human above years of age, such as above, 50, such as above 60 such as above 70 or such as above 80.

In one embodiment, the compound of the present invention is administered as a part of a pharmaceutical composition.

Thus a second aspect of the present invention is to provide a pharmaceudical composition comprising one or more of the compounds of the present invention.

The compound and the composition of the present invention can be in different forms, dry powder, aqueous solution, gel.

In one embodiment of the present invention the compound is an aqueous solution, gel or powder, preferably in an aqueous solution.

Food Ingredients and Food Products

The compounds or the composition according to the present invention can be comprised in a food ingredient.

Thus, an aspect of the present invention relates to a food ingredient comprising the compound or the composition according to the invention. Further, the food ingredient according to the invention may be part of a food product.

Thus, an aspect of the present invention relates to a food product comprising a food ingredient according to the present invention.

In one embodiment of the present invention, the food is selected from the group consisting of a nutraceutical, a food supplement, a dietary supplement, a feed, bar, sugar bar, protein bar, powder, gel, beverage, drink, yoghurt, chewing gum, dairy product, sports drink, confectionary product, ice cream, capsule, tablet, sachet, and pouch.

Non-Therapeutic Uses

The compounds or the compositions according to the invention may be used in a non-therapeutic treatment.

Thus, one aspect of the present invention relates to the use of the compound or composition according to the invention, to reduce free fatty acids circulating in the blood plasma of a subject, in the non-therapeutic treatment of muscle impairment fatigue or improve motor function.

In one embodiment, the compounds for use to reduce free fatty acids circulating in the blood plasma of a subject, in the non-therapeutic treatment of muscle impairment or fatigue, said compound is not DiLa.

Thus, one aspect of the present invention relates to the use of the compound or composition according to the invention, to suppressing appetite, treating obesity, promoting weight loss, preventing, alleviating and/or treating sarcopenia, maintaining a healthy weight or decreasing the ratio of fat to lean muscle.

In one embodiment of the present invention, the compound or composition is for the non-therapeutic treatment of cardiac muscle fatigue, skeletal muscle fatigue, and/or improvement of motor function or for promoting alertness or improving cognitive function in a subject.

Process

The compound can be produced either through synthesis as described in examples 1-3 and 13 or through chemoenzymatic synthesis as seen in examples 11 and 12. Thus, in one aspect the invention relates to a process for producing a compound according to the invention, the process comprising a) providing a compound of formula XLI;

(XLI)

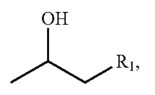

wherein $R_1$ is $CH_2OH$ or OH;

b) reacting said compound from step a) with ethyl lactate, such as (S)-(−)-ethyl lactate in the presence of a Lipase; and c) providing a compound according to the invention.

In one embodiment, the process according to the invention for producing the compounds X and XI comprises a) providing a compound of formula XLII;

(XLII)

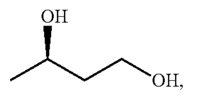

b) reacting said compound from step a) with ethyl lactate, such as (S)-(−)-ethyl lactate in the presence of a Lipase; and c) providing a compound according to formula X-XI.

In another embodiment, the process according to the invention for producing the compounds XIV and XV comprises a) providing a compound of formula XLIII;

(XLIII)

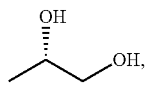

b) reacting said compound from step a) with ethyl lactate, such as (S)-(−)-ethyl lactate in the presence of a Lipase; and c) providing a compound according to formula XIV-XV.

In yet another embodiment, the process according to the invention for producing the compounds XXVI and XXVII comprises a) providing a compound of formula XLIV;

(XLIV)

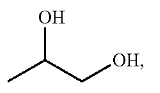

b) reacting said compound from step a) with Ethyl 3-hydroxybutyrate, such as ethyl (R)-(−)-3-hydroxybutyrate in the presence of a Lipase; and c) providing a compound according to formula XXVI and XXVII.

In one embodiment the process further comprises a step d) of purifying the provided compounds, such as by filtering, destillation and/or flash column chromatography (FCC).

In another embodiment the Lipase is immobilized on a solid support such as on beads.

Lipases catalyze the hydrolysis of triacylglycerols into glycerol and free fatty acids. *Candida antarctica* lipase B (CALB) possesses wide substrate specificity, high activity and high enantioselectivity, hence it is considered as a major enzyme in biotechnology. It also has the capability to perform in aqueous and non-aqueous reaction environments. CALB may be used in transesterification, kinetic resolution and polymerization reactions.

Thus, in another embodiment, the Lipase is selected from the group consisting of Lipase B, Lipase B *Candida Antarctica* immobilized on Immobead 150, Novozym® 435, CALB, CALB lipase immobilised on an hydrophobic carrier, Lipozyme TL IM and Lipozyme® RM, 1,3 specific lipase.

In a preferred embodiment, the Lipase is Lipase B, more preferably CALB or Novozym 435.

In the example section (examples 11 and 12), Lipase B *Candida Antarctica* immobilized on Immobead 150 has been used.

Other Aspects

US2011237666 A1 for example discloses numerous physical states or diseases which may be treated with ketone compounds.

An aspect of the invention relates to a method of treating a condition which is caused by, exacerbated by or associated with elevated plasma levels of free fatty acids in a human or animal subject, which method comprises administering to the subject a compound, composition or pharmaceutical composition according to the invention.

Another aspect of the invention relates to a method of treating a condition where weight loss or weight gain is implicated, which method comprises administering to a subject in need thereof a compound, composition or pharmaceutical composition according to the invention.

A further aspect of the invention relates to a method of suppressing appetite, treating obesity, promoting weight loss, maintaining a healthy weight or decreasing the ratio of fat to lean muscle, which method comprises administering to a subject in need thereof a compound, composition or pharmaceutical composition according to the invention.

Yet an aspect of the invention relates to a method of preventing or treating a condition selected from cognitive dysfunction, a neurodegenerative disease or disorder, muscle impairment, fatigue and muscle fatigue, which method comprises administering to a subject in need thereof a compound, composition or pharmaceutical composition according to the invention.

An aspect relates to a method of treating a patient suffering from a condition selected from diabetes, hyperthyroidism, metabolic syndrome X, or for treating a geriatric patient, which method comprises administering thereto a compound, composition or pharmaceutical composition according to the invention.

Yet a further aspect relates to a method of treating, preventing, or reducing the effects of, neurodegeneration, free radical toxicity, hypoxic conditions or hyperglycaemia which method comprises administering to a subject in need thereof a compound, composition or pharmaceutical composition according to the invention. In an embodiment, the neurodegeneration is caused by aging, trauma, anoxia or a neurodegenerative disease or disorder.

An aspect also relates to a method of preventing or treating a neurodegenerative disease or disorder selected from Alzheimer's disease, Parkinson's disease, amyotrophic lateral sclerosis, epilepsy, astrocytoma, glioblastoma and Huntington's chorea, which method comprises administering to a subject in need thereof a compound, composition or pharmaceutical composition according to the invention.

Another aspect relates to a method of promoting alertness or improving cognitive function in a subject, which method comprises administering to said subject a compound, composition or pharmaceutical composition according to the invention. An aspect also relates to the use of a compound or composition according to the invention to reduce free fatty acids circulating in the blood plasma of a subject, in the non-therapeutic treatment of muscle impairment or fatigue.

Yet an aspect relates to the use according to the use of a compound or composition according to the invention, wherein the compound or composition is for the non-therapeutic treatment of cardiac muscle fatigue or skeletal muscle fatigue.

EXAMPLES

Example 1

Synthesis of the LaKe Compounds 3 and 4 (Structure X and XI)

The LaKe compounds are prepared according to the following procedure. Synthesis of the compounds X and XI:

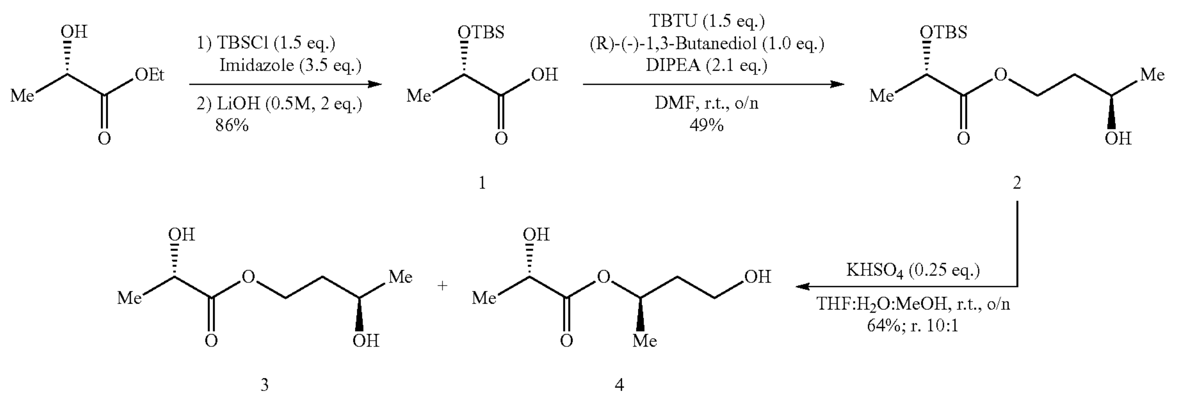

1

2

3 + 4

(S)-2-((tert-butyldimethylsilyl)oxy)propanoic acid (1):

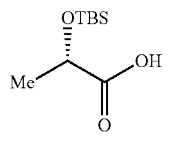

1

To a solution of ethyl (S)-2-hydroxypropionate (14.4 mL, 127 mmol, 1.0 eq.) in anhydrous DMF (250 mL) was added TBSCI (28.7 g, 191 mmol, 1.5 eq.) followed by imidazole (30.3 g, 445 mmol, 3.5 eq.). The mixture was stirred at r.t. for 3 hours before diluted with sat. aq. NaCl and extracted with EtOAc. The organic layers were combined and washed with 5% aq. HCl and sat. aq. NaCl. The organic layer was then dried over $Na_2SO_4$, filtered and concentrated to afford ethyl (S)-2-(tert-butyldimethylsilyloxy)propanoate (29.5 g, quant.). Product formation was determined with 1 H NMR analysis. No further purification was performed as the product was subjected directly into the following step.

$R_f$ (Pentane/EtOAc 98:2, $KMnO_4$).

$^1$H NMR (400 MHz, CDC13) $\delta_H$ 4.34-4.26 (q, J=6.74 Hz, 1H), 4.24-4.11 (m, 2H), 1.41-1.36(d, J=6.75 Hz, 3H), 1.30-1.24 (t, J=7.16 Hz, 3H), 0.91-0.87 (s, 9H), 0.11-(d, J=11.99 Hz, 6H).

To a solution of (S)-2-(tert-butyldimethylsilyloxy)propanoate (29.5 g, 127 mmol, 1.0 eq.) in THF (400 mL) at 0° C. was added a cooled aq. LiOH solution (508 mL, 0.5 M). The reaction mixture was stirred at r.t. for 5 hours before concentrated to half of the original volume and extracted with $Et_2O$. The organic extracts were combined before extracted with a sat. aq. $NaHCO_3$ solution. The aqueous layers were combined and acidified with a 1 M aq. $KHSO_4$ solution to reach pH 3-4. Afterwards, the aqueous solution was extracted thoroughly with $Et_2O$ and the organic layers were combined, dried over $Na_2SO_4$ and concentrated to afford (S)-2-(tert-butyldimethylsilyloxy)propanoic acid (22.3 g, 86%) as an oil. Product formation was determined with 1 H NMR analysis (1 H NMR values are in accordance with reported values)[1].

$^1$H NMR (400 MHz, $CDCl_3$) $\delta_H$ 4.38-4.33 (q, J=6.88 Hz, 1H), 1.46-1.45 (d, J=6.80 Hz,3H), (m, 9H), 0.16-0.12 (s, 6H).

(R)-3-Hydroxybutyl (S)-2-(((tert)-butyldimethylsilyl)oxy)propanoate (2):

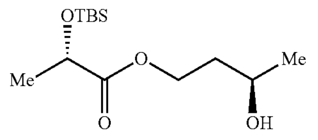

2

(S)-2-(tert-butyldimethylsilyloxy)propanoic acid (8.42 g, 41.2 mmol, 1.0 eq.), TBTU (19.9 g, 61.8 mmol, 1.5 eq.) and DIPEA (15.1 mL, 86.5 mmol, 2.1 eq.) were dissolved in anhydrous DMF (150 mL) and the mixture was stirred at r.t. for 1 hour. (R)-(−)-1,3-butanediol (3.68 mL, 41.2 mmol, 1.0 eq.) in anhydrous DMF (10 mL) was then added and the reaction mixture was stirred o/n. at ambient temperature. The reaction mixture was diluted with $CH_2Cl_2$ and the resulting mixture was washed with 1 M aq. HCl, aq. $NaHCO_3$ and water sequentially. The organic layers were then combined, dried over $Na_2SO_4$, filtered and concentrated to afford the crude product. FCC (pentane/EtOAc=95:5 to 85:15) was performed to afford the pure product (2) (5601 mg, 49%).

$R_f$ 0.38 (Pentane/EtOAc 8:2, $KMnO_4$).

$^1$H NMR (400 MHz, $CDCl_3$) $\delta_H$ 4.42-4.30 (m, 2H), 4.21-4.16 (m, 1H), 3.93-3.84 (m, 1H), 2.00-1.97 (d, J=4.27 Hz, 1H), 1.85-1.69 (m, 2H), 1.42-1.38 (d, J=6.79 Hz, 3H), 1.24-1.21 (d, J=6.27 Hz, 3H), 0.91-0.89 (s, 9H), 0.11-0.07 (d, J=10.17 Hz, 6H).

$^{13}$C NMR (101 MHz, $CDCl_3$) $\delta_C$ 174.6, 68.6, 65.1, 62.3, 38.2, 25.9, 23.6, 21.5, 18.4, −4.8, 5.1.

IR (Neat)

$u_{max}$/cm$^{-1}$ 3440, 2930, 2858, 1737, 1463, 1373, 1256, 1140.

HRMS

[M+Na]+=299.1649; found: 299.1644.

$[\alpha]^{24.0}_{D}$

−34.6° (C=10 mg/mL, $CHCl_3$).

(R)-3-Hydroxybutyl (S)-2-hydroxypropanoate (3) and (R)-4-hydroxybutan-2-yl (S)-2-hydroxypropanoate (4):

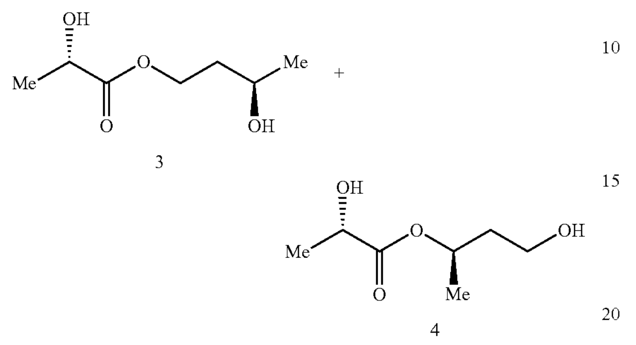

To a stirred solution of TBDMS ether (5612 mg, 20.3 mmol, 1.0 eq.) in $THF:H_2O:MeOH$ (2.5:2.5:1, 100 mL) was added $KHSO_4$ (691 mg, 5.08 mmol, 0.25 eq.) and the mixture was stirred at r.t. o/n. MeOH was removed under reduced pressure and water was added before extracted with EtOAc. The organic layers were collected and dried over $Na_2SO_4$, filtered and concentrated. The crude product was purified with FCC (Pentane/EtOAc=1:1) to afford the desired products (2100 mg, 68%, r. 10:1).

$R_f$ (Pentane/EtOAc 1:1, CAM).

$^1H$ NMR

3: (400 MHz, $CDCl_3$) $\delta_H$ 4.46-4.37 (m, 1H), 4.32-4.23 (m, 2H), 3.95-3.85 (m, 1H), 2.81-2.79 (d, J=5.28 Hz, 1H), 1.87-1.71 (m, 3H), 1.44-1.39 (d, J=6.97 Hz, 3H), 1.27-1.22 (d, J=6.53 Hz, 3H).

4: (400 MHz, $CDCl_3$) $\delta_H$ 5.25-5.17 (m, 1H), 4.46-4.37 (m, 1H), 3.74-3.57 (m, 2H), 1.87-1.71 (m, 2H), 1.44-1.39 (d, J=6.97 Hz, 3H), 1.33-1.30 (d, J=6.22 Hz, 3H).

$^{13}C$ NMR

3: (101 MHz, $CDCl_3$) $\delta_C$ 176.1, 66.9, 64.9, 63.0, 38.0, 23.8, 20.6.

IR (Neat)

$\nu_{max}/cm^{-1}$ 3380, 2971, 1732, 1457, 1375, 1274, 1209, 1130, 1049.

HRMS

[M+Na]+=185.0784; found: 185.0783.

Example 2

Synthesis of the LaKe Compounds 10 and 11 (Structure XII and XIII)

The LaKe compounds are prepared according to the following procedure.

Synthesis of the compounds XII and XIII:

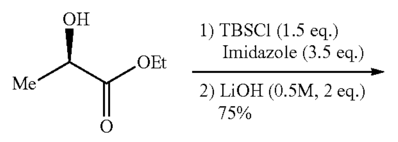

-continued

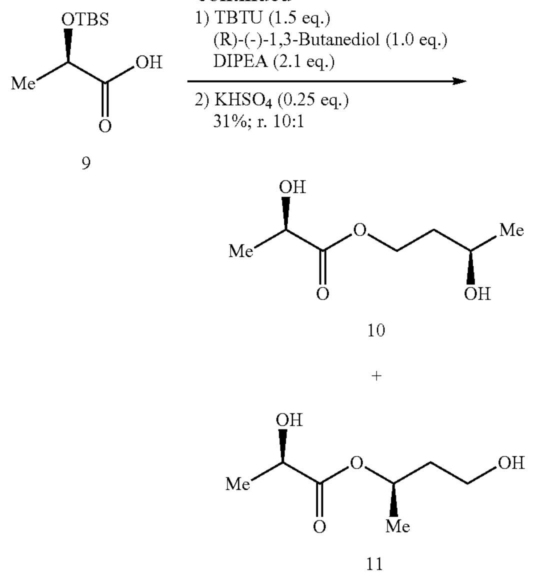

(R)-2-((tert-butyldimethylsilyl)oxy)propanoic acid (9):

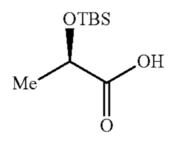

To a solution of ethyl (R)-2-hydroxypropionate (6.74 mL, 59.3 mmol, 1.0 eq.) in anhydrous DMF (100 mL) was added TBSCI (13.4 g, 89 mmol, 1.5 eq.) followed by imidazole (14.1 g, 208 mmol, 3.5 eq.). The mixture was stirred at r.t. for 3 hours before diluted with sat. aq. NaCl and extracted with EtOAc. The organic layers were combined and washed with 5% aq. HCl and sat. aq. NaCl. The organic layer was then dried over Na2SO4, filtered and concentrated to afford ethyl (R)-2-(tert-butyldimethylsilyloxy)propanoate (13.7 g, quant.). Product formation was determined with 1 H NMR analysis. No further purification was performed as the product was subjected directly into the following step.

$R_f$ 0.41 (Pentane/EtOAc 98:2, $KMnO_4$).

$^1H$ NMR (400 MHz, $CDCl_3$) $\delta_H$ 4.34-4.26 (q, J=6.74 Hz, 1H), 4.24-4.11 (m, 2H), 1.41-1.36 (d, J=6.75 Hz, 3H), 1.30-1.24 (t, J=7.16 Hz, 3H), 0.91-0.87 (s, 9H), 0.11-0.04 (d, J=11.99 Hz, 6H).

To a solution of the (R)-2-(tert-butyldimethylsilyloxy) propanoate (13.7 g, 59.3 mmol, 1.0 eq.) in THF (400 mL) at 0° C. was added a cooled aq. LiOH solution (400 mL, 0.3 M). The reaction mixture was stirred at r.t. for 5 hours before concentrated to half of the original volume and extracted with $Et_2O$. The organic extracts were combined before extracted with a sat. aq. $NaHCO_3$ solution. The aqueous layers were combined and acidified with a 1 M aq. $KHSO_4$ solution to reach pH≈3-4. Afterwards, the aqueous solution was extracted thoroughly with $Et_2O$ and the organic layers were combined, dried over $Na_2SO_4$ and concentrated to afford (R)-2-(tert-butyldimethylsilyloxy)propanoic acid (9085 mg, 75%) as an oil. Product formation was determined with 1 H NMR analysis (1 H NMR values are in accordance with reported values)[2].

$^1H$ NMR (400 MHz, $CDCl_3$) $\delta_H$ 4.38-4.33 (q, J=6.88 Hz, 1H), 1.46-1.45 (d, J=6.80 Hz, 3H), 0.94-0.90 (m, 9H), 0.16-0.12 (s, 6H).

(R)-3-Hydroxybutyl (R)-2-hydroxypropanoate (10) and (R)-4-hydroxybutan-2-yl (R)-2-hydroxypropanoate (11):

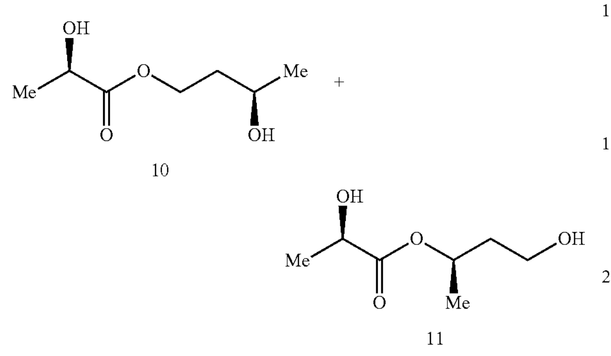

10

11

(R)-2-((tert-butyldimethylsilyl)oxy)propanoic acid (8.99 g, 44.0 mmol, 1.0 eq.), TBTU (21.3 g, 66.0 mmol, 1.5 eq.) and DIPEA (16.1 mL, 92.4 mmol, 2.1 eq.) were dissolved in anhydrous DMF (175 mL) and the mixture was stirred at r.t. for 1 hour. (R)-(−)-1,3-butanediol (3.93 mL, 44.0 mmol, 1.0 eq.) in anhydrous DMF (10 mL) was then added and the reaction mixture was stirred o/n. at ambient temperature. The reaction mixture was diluted with $CH_2Cl_2$ and the resulting mixture was washed with 1 M aq. HCl, aq. $NaHCO_3$ and water sequentially. The organic layers were then combined, dried over $Na_2SO_4$, filtered and concentrated to afford the crude product. FCC (pentane/EtOAc=95:5 to 85:15) was performed to afford the pure product (5576 mg, 46%).

$R_f$ (Pentane/EtOAc 8:2, $KMnO_4$).

$^1H$ NMR (400 MHz, $CDCl_3$) $\delta_H$ 4.44-4.36 (m, 1H), 4.36-4.29 (q, J=6.58 Hz, 1H), 4.20-4.13 (m, 1H), 3.93-3.82 (m, 1H), 2.01-1.96 (d, J=4.44 Hz, 1H), 1.86-1.67 (m, 2H), 1.42-1.38 (d, J=6.69 Hz, 3H), 1.25-1.20 (d, J=6.21 Hz, 3H), 0.93-0.87 (s, 9H), 0.11-0.07 (d, J=10.35 Hz, 6H).

IR (Neat)

$u_{max}/cm^{-1}$ 1 3449, 2958, 2930, 2900, 2858, 1736, 1253, 1138.

HRMS $[M+Na]^+$=299.1649; found: 299.1658.

+17.1° (C=8.5 mg/mL, $CHCl_3$).

To a stirred solution of TBDMS ether (5576 mg, 20.2 mmol, 1.0 eq.) in THF:$H_2O$:MeOH (2.5:2.5:1, 100 mL) was added $KHSO_4$ (668 mg, 5.05 mmol, 0.25 eq.) and the mixture was stirred at r.t. o/n. MeOH was removed under reduced pressure and water was added before extracted with EtOAc. The organic layers were collected and dried over $Na_2SO_4$, filtered and concentrated. The crude product was purified with FCC (Pentane/EtOAc=1:1) to afford the desired products (2110 mg, 64%, r. 10:1).

$R_f$ 0.19 (Pentane/EtOAc 1:1, CAM).

$^1H$ NMR (400 MHz, $CDCl_3$) $\delta_H$ 4.49-4.38 (m, 1H), 4.33-4.20 (m, 2H), 3.95-3.83 (m, 1H), 2.82-2.74 (d, J=4.96 Hz, 1H), 1.98-1.61 (m, 3H), 1.44-1.39 (d, J=6.92 Hz, 3H), 1.27-1.22 (d, J=6.22 Hz, 3H).

11: (400 MHz, $CDCl_3$) OH 5.25-5.17 (m, 1H), 4.49-4.38 (m, 1H), 3.71-3.64 (m, 1H), 3.63-3.54 (m, 1H), 1.98-1.61 (m, 3H), 1.44-1.39 (d, J=6.92 Hz, 3H), 1.34-1.20 (d, J=6.21 Hz, 3H).

$^{13}C$ NMR

10: (101 MHz, $CDCl_3$) $\delta_C$ 176.1, 66.9, 64.9, 63.0, 37.9, 23.7, 20.5.

IR (Neat)

$u_{max}/cm^{-1}$ 1 3377, 2971, 2901, 1732, 1376, 1209, 1128, 1079, 1049.

HRMS $[M+Na]^+$=185.0784; found: 185.0790.

Example 3

Synthesis of the DiLa Compounds 7 and 8 (Structure XIV and XV)

Synthesis of the compounds XIV and XV:

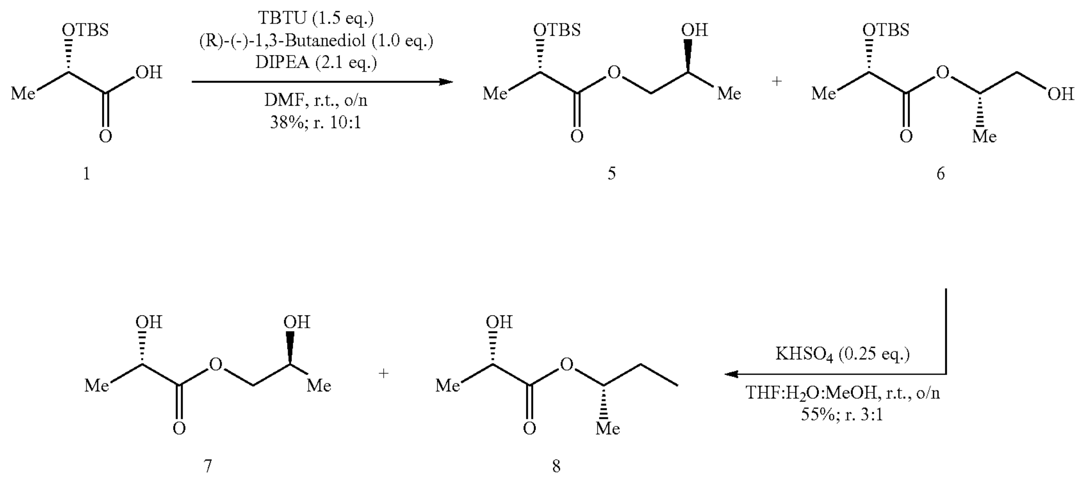

1 5 6 7 8

(S)-2-Hydroxypropyl (S)-2-((tert-butyldimethylsilyl)oxy) propanoate (5) and (S)-1-hydroxypropan-2-yl (S)-2-((tert-butyldimethylsilyl)oxy) propanoate (6):

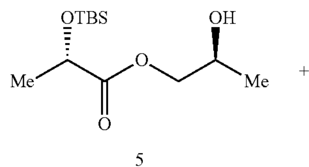

5

+

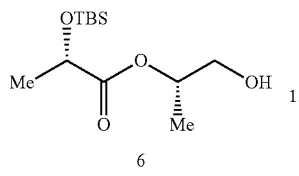

6

(S)-2-(tert-butyldimethylsilyloxy)propanoic acid (5.80 g, 28.4 mmol, 1.0 eq.), TBTU (13.7 g, 42.6 mmol, 1.5 eq.) and DIPEA (10.4 mL, 59.6 mmol, 2.1 eq.) were dissolved in anhydrous DMF (80 mL) and the mixture was stirred at r.t. for 1 hour. (S)-(−)-1,2-propanediol (2.08 mL, 28.4 mmol, 1.0 eq.) in anhydrous DMF (10 mL) was then added and the reaction mixture was stirred o/n. at ambient temperature. The reaction mixture was diluted with $CH_2Cl_2$ and the resulting mixture was washed with 1 M aq. HCl, aq. $NaHCO_3$ and water sequentially. The organic layers were then combined, dried over $Na_2SO_4$, filtered and concentrated to afford the crude product. FCC (pentane/EtOAc=85:15) was performed to afford 5 and 6 (2850 mg, 38% ; r. 10:1).

$R_f$ 0.14 (Pentane/EtOAc 9:1, $KMnO_4$).

$^1$H NMR

5: (400 MHz, $CDCl_3$) $\delta_H$ 4.40-4.32 (q, J=6.79 Hz, 1H), 4.16-4.10 (dd, J=10.79 Hz, 2.76 Hz, 1H), 4.08-4.01 (m, 1H), 4.01-3.94 (dd,J=10.77 Hz, 7.13 Hz, 1H), 2.14-2.09 (d, J=3.47 Hz, 1H), 1.44-1.39 (d, J=6.72 Hz, 3H), 1.23-1.18 (d, J=6.26 Hz, 3H), 0.92-0.88 (s, 9H), 0.12-0.05 (d, J=9.51 Hz, 6H).

6: (400 MHz, $CDCl_3$) $\delta_H$ 5.05-4.96 (m, 1H), 4.34-4.29 (q, J=6.69 Hz, 1H), 3.71-3.58 (m, 2H), 1.96-1.91 (t, J=6.05 Hz, 1H), 1.41-1.38 (d, J=6.72 Hz, 3H), 1.26-1.23 (d, J=6.56 Hz, 3H), 0.92-0.88 (s, 9H), 0.12-0.05 (d, J=9.51 Hz, 6H).

$^{13}$C NMR

5: (101 MHz, $CDCl_3$) $\delta_C$ 174.3, 70.0, 68.5, 66.2, 25.8, 21.4, 19.2, 18.4, −4.8, −5.1.

IR (Neat)

$u_{max}$/cm $^{-1}$ 1 3508, 2953, 2931, 2887, 2857, 1739, 1472, 1254, 1203, 1141, 1061.

HRMS $[M+Na]^+$=285.1493; found: 285.1497.

(S)-2-Hydroxypropyl (S)-2-hydroxypropanoate (7) and (S)-1-hydroxypropan-2-yl (S)-2-hydroxypropanoate (8):

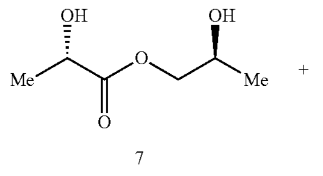

7

+

-continued

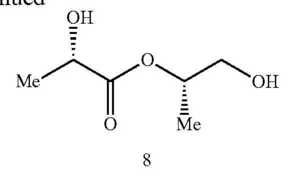

8

To a stirred solution of TBDMS ether (2834 mg, 10.8 mmol, 1.0 eq.) in THF:$H_2O$:MeOH (2.5:2.5:1, 50 mL) was added $KHSO_4$ (368 mg, 2.70 mmol, 0.25 eq.) and the mixture was stirred at r.t. o/n. MeOH was removed under reduced pressure and water was added before extracted with EtOAc. The organic layers were collected and dried over $Na_2SO_4$, filtered and concentrated. The crude product was purified with FCC (Pentane/EtOAc=1:1 to 4:6) to afford the desired products (880 mg, 55%, r. 3:1).

$R_f$ (Pentane/EtOAc 1:1, $KMnO_4$).

$^1$H NMR

7: (400 MHz, $CDCl_3$) $\delta_H$ 4.37-4.29 (q, J=6.62 Hz, 1H), 4.18-4.12 (dd, J=10.70 Hz, 2.54 Hz, 1H), 4.08-4.00 (m, 1H), 4.00-3.94 (dd,J=10.71 Hz, 7.28 Hz, 1H), 3.90-3.83 (s, 1H), 3.38-3.30 (s, 1H), 1.44-1.40 (d, J=6.99 Hz, 3H), 1.21-1.17 (d, J=6.14 Hz, 3H).

8: (400 MHz, $CDCl_3$) $\delta_H$ 5.06-4.97 (m, 1H), 4.30-4.24 (q, J=6.81 Hz, 1H), 3.86-3.80 (m, 1H), 3.70-3.63 (d, J=11.81 Hz, 2H), 3.63-3.53 (m, 1H), 3.28-3.19 (s, 1H), 1.42 1.38 (d, J=6.72 Hz, 3H), 1.25-1.21 (d, J=6.43 Hz, 3H).

$^{13}$C NMR

7: (101 MHz, $CDCl_3$) $\delta_C$ 175.3, 70.2, 67.2, 65.8, 20.4, 19.0.

8: (101 MHz, $CDCl_3$) $\delta_C$ 175.3, 73.1, 67.4, 65.3, 20.4, 16.1.

IR (Neat)

$u_{max}$/cm$^{-1}$ 3391, 2984, 1734, 1455, 1374, 1213, 1130, 1054.

HRMS $[M+Na]^+$=171.0628; found: 171.0629.

Example 4

Design of Animal Experiment

Preparation of the Drug

The LaKe ester (structure X and XI) was diluted in physiological saline solution (0.9% NaCl) and administered as a single bolus of 2 mL, per oral dose. The dose of 4500 mg/kg was based on a previous pilot series (data not shown). Placebo animals received a single bolus of 2 mL physiological saline solution (0.9% NaCl).

Animal setup:

Male Sprague Dawley rats (300-350 g, Taconic, Ry, Denmark) were kept for acclimatization at a constant temperature of 23° C., with a 12 h light-dark cycle and with unlimited access to food and water. All animal handling was in accordance with national guidelines in Denmark and the Guide for the Care and Use of Laboratory Animals 1 and all experiments conformed to Danish Law (Act. No. 1306 of 23/11/2007).

The rats were randomly selected to receive either LaKe (n=8) or placebo (n=8). Rats were anaesthetised in an induction chamber with 8% Sevoflurane (Sevorane®, AbbVIE A/S, Copenhagen, Denmark) mixed with oxygen saturated atmospheric air (flow: 2.0 L/min).

Upon achieved anaesthesia, the rats were intubated and connected to a mechanical ventilator (Ugo Basile 7025 rodent ventilator, Comerio, Varese, Italy) with an adjusted flow of 1.0 L/min with 3.5% Sevoflurane. Body temperature was kept at a constant 37° C.±1° C. with a temperature probe (UNO, Zevenaar, Holland). A PTFE coated flexible orogastric tube (Fuchigami, Japan) was placed and the rat was left for stabilization for 15 minutes.

After stabilization a baseline blood sample was collected from the rat tail vein before administration of LaKe or placebo.

Following the baseline blood sample, a bolus of LaKe solution or placebo was administered via the orogastric tube to the animals. Every 15 minutes for a period of two hours, blood samples (200 uL each) were collected in microvettes (sarstedt—20.1280.100) and was left to coagulate for 30 minutes followed by centrifugation at 4° C., 1500G for 20 minutes. Serum was collected and stored at −80° C. for further analysis.

Statistical Analysis

Based on own experience and reports by other research groups, a sample size of n=8 was considered adequate to identify a treatment effect. All results are expressed as mean±SD unless otherwise stated. Differences in concentrations were analysed using two-way ANOVA with Bonferroni post hoc correction. All analyses were performed using GraphPad Prism 8.2.0 (Graph Pad Software, CA, USA). $P<0.05$ was considered statistically significant.

Example 5

Quantification of BHB and Lactate in Rat Serum—LaKe (Structure X and XI)

The concentration of BHB and lactate is determined in the blood samples isolated from the rats according to example 4. Rat serum isolated every 15 minutes for a 2 hours were analyzed. The quantification was done on LC-MS/MS using isotopically labeled internal standards (7).

FIG. 1A: BHB concentration (μM) in rat serum isolated from two groups of rats, one treated with LaKe, one treated with the control.

FIG. 1B: Lactate concentration (μM) in rat serum isolated from two groups of rats, one treated with LaKe, one treated with the control.

Conclusion

Here we show that treatment with LaKe (structure X and XI), compared to the control (physiological saline 0.9%) gives rise to an increased serum concentration of both BHB and lactate in rats following oral administration.

Example 6

Effect of the Lake Ester (Structure X and XI) on Free Fatty Acids

The concentration of free-fatty acids (FFA) was determined in the blood samples isolated from the rats according to example 4. The level of FFA in blood reflects ongoing lipolysis and high levels of FFA induce insulin resistance; conversely agents that lower the level of free fatty acids in the blood can be used therapeutically to increase insulin sensitivity in people with type 2 diabetes and the metabolic syndrome.

Concentrations of non-esterified free fatty acids (NEFA) were measured using a NEFA-HR(2) kit (Wako, Chemicals Gmbh). Absorbance was measured by spectrometry (PHERAstar FS, BMG LABTECH, Ortenberg, Germany).

Figure 2:
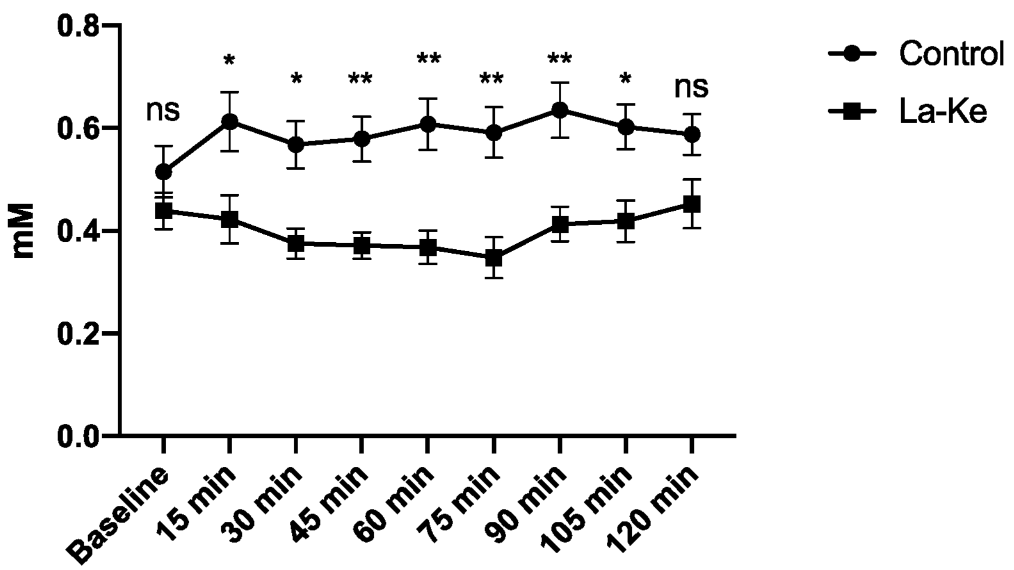
FIG. 2 shows the concentration (μM) of non-esterified free fatty acids in rat serum over time following oral administration of either compound X and XI (LaKe) or physiological saline solution (0.9% NaCl) as a control to rats.

FIG. 2: The concentration (mM) of free fatty acids in the serum was strongly decreased in the rats treated with LaKe compared to rats treated with the control (physiological saline 0.9%).

Conclusion

Here, we show that oral administration of LaKe (structure X and XI) leads to a decreased concentration of FFA in rat serum compared to the control.

Example 7

Quantification of BHB and Lactate in Rat Serum—KeLa (Structure XXVI and XXVII)

The concentration of BHB and lactate is determined in the blood samples isolated from the rats according to example 4, with the difference that KeLa (structure XXVI and XXVII) was used. Rat serum isolated every 15 minutes for a 2 hours were analyzed. The quantification was done on LC-MS/MS using isotopically labeled internal standards (7).

Figure 3:
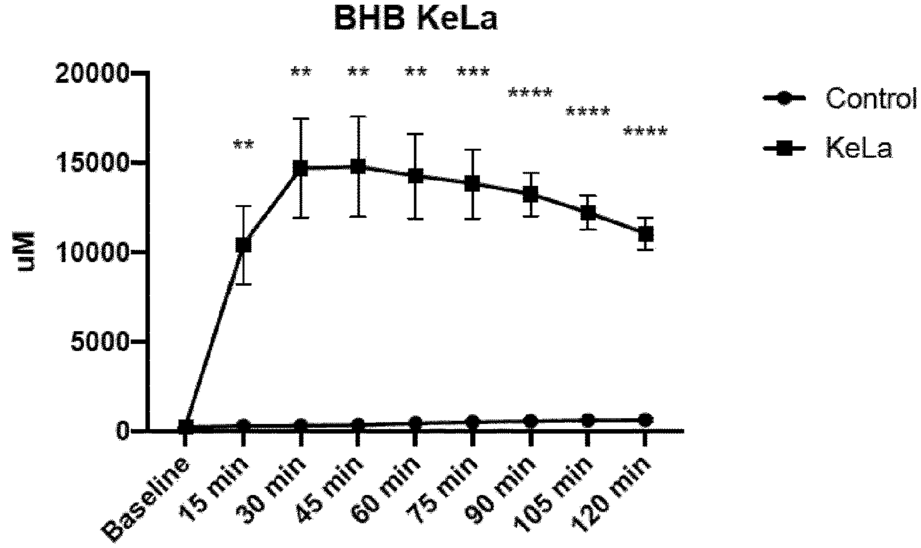
FIG. 3 shows the concentration (μM) of BHB (FIG. 3A) and lactate (FIG. 3B) in rat serum over time, following oral administration of either compound XXVI and XXVII (KeLa) or physiological saline solution (0.9% NaCl) as a control to rats. The increase in lactate for the KeLa ester is statistically significant from 90 min and onwards.
Figure 3:
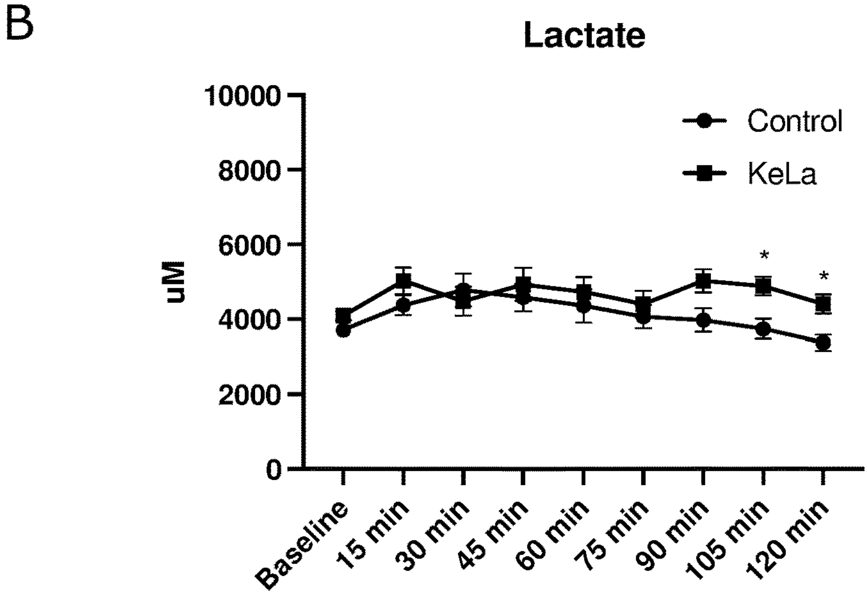

FIG. 3A: BHB concentration (μM) in rat serum isolated from two groups of rats, one treated with KeLa, one treated with the control.

FIG. 3B: Lactate concentration (μM) in rat serum isolated from two groups of rats, one treated with KeLa, one treated with the control. The increase in lactate for the KeLa ester is statistically significant from 90 min and onwards.

Conclusion

Here we show that treatment with KeLa (structure XXVI and XXVII) compared to the control (physiological saline 0.9%) gives rise to an increased serum concentration of both BHB and lactate in rats following oral administration.

Example 8

Quantification of BHB and Lactate in Rat Serum—DiLa (Structure XIV and XV)

The concentration of BHB and lactate is determined in the blood samples isolated from the rats according to example 4, with the difference that DiLa (structure XIV and XV) was used. Rat serum isolated every 15 minutes for a 2 hours were analyzed. The quantification was done on LC-MS/MS using isotopically labeled internal standards (7).

Figure 4:
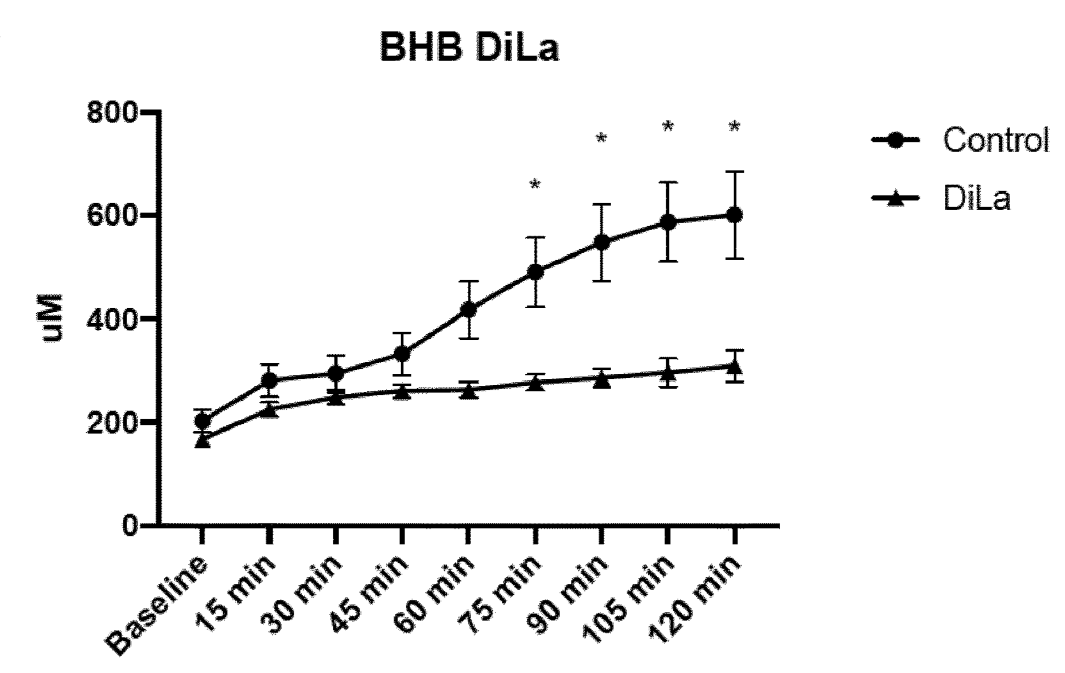
FIG. 4 shows the concentration (μM) of BHB (FIG. 4A) and lactate (FIG. 4B) in rat serum over time, following oral administration of either compound XIV and XV (DiLa) or physiological saline solution (0.9% NaCl) as a control to rats.
Figure 4:
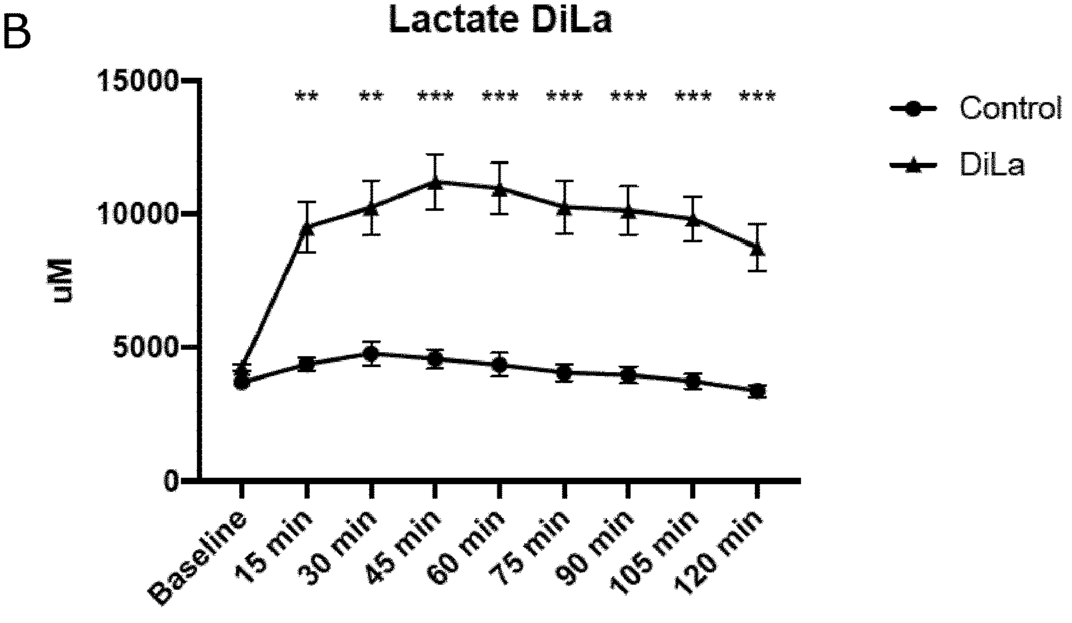

FIG. 4A: BHB concentration (μM) in rat serum isolated from two groups of rats, one treated with DiLa, one treated with the control.

FIG. 4B: Lactate concentration (μM) in rat serum isolated from two groups of rats, one treated with DiLa, one treated with the control.

Conclusion

Here we show that treatment with DiLa (structure XIV and XV) compared to the control (physiological saline 0.9%) gives rise to an increased serum concentration of lactate in rats following oral administration.

The DiLa ester appears not to release BHB directly (only lactate), but the data suggests an inhibition of BHB-mobilization relative to control during the experiment. This is compatible with a distinct inhibition of ketone formation (ketogenesis) in the liver, since levels of FFA, which are ketone body precursors, if anything were increased after DiLa ester administration.

Example 9

Effect of the KeLa Ester (Structure XXVI and XXVII) on Free Fatty Acids

The concentration of free-fatty acids (FFA) was determined in the blood samples isolated from the rats according to example 4, with the difference that KeLa (structure XXVI and XXVII) was used. The level of FFA in blood reflects ongoing lipolysis and high levels of FFA induce insulin resistance; conversely agents that lower the level of free fatty acids in the blood can be used therapeutically to increase insulin sensitivity in people with type 2 diabetes and the metabolic syndrome.

Concentrations of non-esterified free fatty acids (NEFA) were measured using a NEFA-HR(2) kit (Wako, Chemicals Gmbh). Absorbance was measured by spectrometry (PHER-Astar FS, BMG LABTECH, Ortenberg, Germany).

Figure 5:
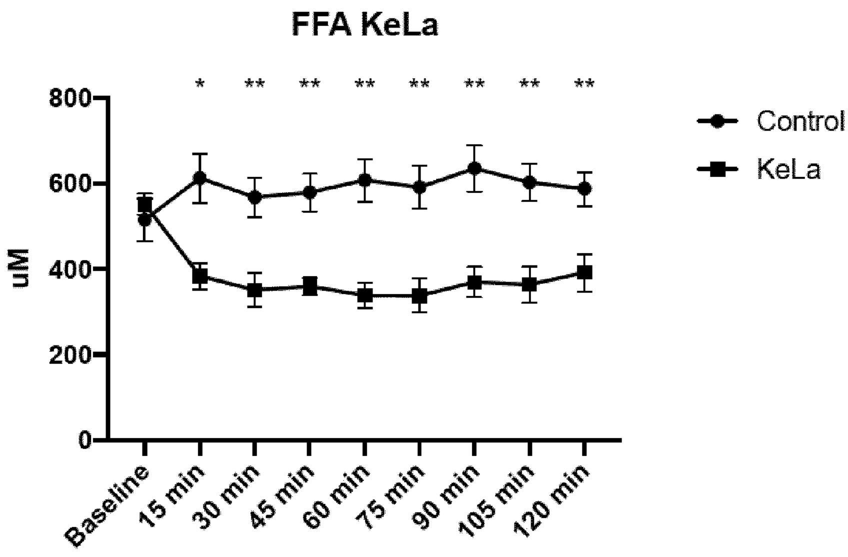
FIG. 5 shows the concentration (μM) of Non-esterified free fatty acids in rat serum over time following oral administration of either compound XXVI and XXVII (KeLa) or physiological saline solution (0.9% NaCl) as a control to rats.

FIG. 5: The concentration (μM) of free fatty acids in the serum was strongly decreased in the rats treated with LaKe compared to rats treated with the control (physiological saline 0.9%).

Conclusion

Here, we show that oral administration of Kela ester (structure XXVI and XXVII) leads to a decreased concentration of FFA in rat serum compared to the control.

Example 10

Effect of DiLa Ester (Structure XIV and XV) on Free Fatty Acids

The concentration of free-fatty acids (FFA) was determined in the blood samples isolated from the rats according to example 4, with the difference that DiLa (structure XIV and XV) was used. The level of FFA in blood reflects ongoing lipolysis and high levels of FFA induce insulin resistance; conversely agents that lower the level of free fatty acids in the blood can be used therapeutically to increase insulin sensitivity in people with type 2 diabetes and the metabolic syndrome.

Concentrations of non-esterified free fatty acids (NEFA) were measured using a NEFA-HR(2) kit (Wako, Chemicals Gmbh). Absorbance was measured by spectrometry (PHER-Astar FS, BMG LABTECH, Ortenberg, Germany).

Figure 6:
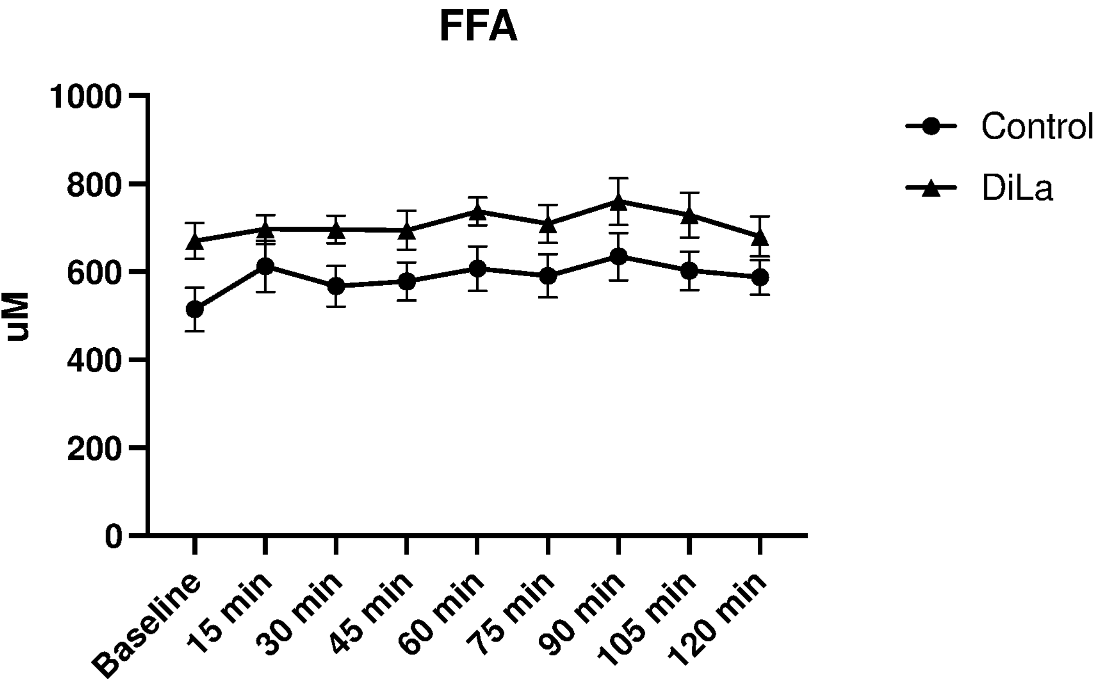
FIG. 6 shows the concentration (μM) of Non-esterified free fatty acids in rat serum over time following oral administration of either compound XIV and XV (DiLa) or physiological saline solution (0.9% NaCl) as a control to rats.

FIG. 6: The concentration (μM) of free fatty acids in the serum was not decreased in the rats treated with DiLa compared to rats treated with the control (physiological saline 0.9%).

Conclusion

Here, we show that oral administration of DiLa ester (structure XIV and XV) do not lead to a decreased concentration of FFA in rat serum compared to the control.

The presented data clearly shows that the DiLa ester results in release of lactate in large amounts (see example 8) and the compound should therefore be useful in any (medical) situation where the ability to increase lactate would be beneficial.

Further, the FFA-data for the DiLa ester, when compared to that from LaKe and KeLa, shows that the lowering of FFA is mainly driven by the BHB-components of LaKe and KeLa.

The DiLa ester may be important in the following scenarios:

when one wishes to exclusively deliver lactate.

The compound may be combined (in different ratios) with other ketone esters, such as 1,3-butanediol diacetoacetate, 1,3-butanediol dihexanoate, 1,3-butanediol, medium chain triglycerides, 3-hydroxybutyl 3-hydroxybutyrate and (3R)-hydroxybutyl (3R)-hydroxybutyrate and/ KeLA and LaKe to achieve a dual delivery of BHB and lactate.

Example 11

Chemoenzymatic Synthesis of L-(−)-lactatic Acid Esters 3 (Structure X) and 4 (Structure XI) (LaKe Esters):

Aim of Study

To provide a Chemoenzymatic synthesis of L-(−)-lactic acid esters 3 and 4 (LaKe esters).

Materials and Methods

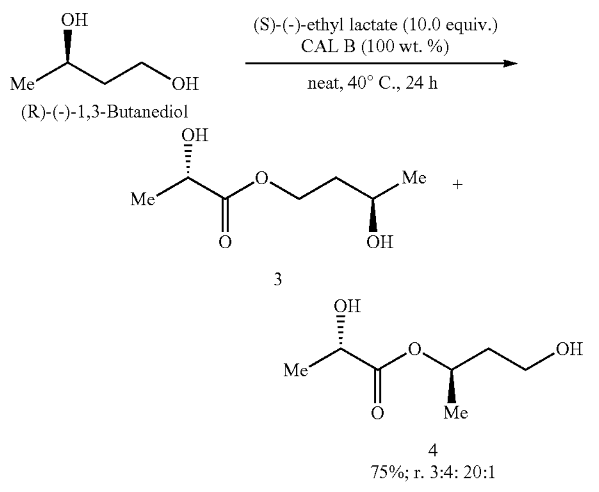

(R)-(-)-1,3-Butanediol

3

+

4

The protocol for the enzymatic synthesis of L-(−)-lactic acid esters 3 and 4 is as follows:

(R)-(−)-1,3-Butanediol (1.50 g, 16.6 mmol, 1.0 equiv.), (S)-(−)-ethyl lactate (19.7 g, 166 mmol, 10.0 equiv.) and Cal B (1.50 g, 100 wt. %) (Lipase B Candida antarctica immobilized on Immobead 150, recombinant from yeast (≈4000 U/g), SIGMA) was placed in a 50 mL flask and heated to 40° C. The mixture was kept at this temperature and stirred carefully (300-350 rpm) for 24 h. The mixture was cooled to rt and filtered under vacuum to remove enzyme beads and the filtrate was concentrated in vacuo. The crude product was subjected to FCC (pentane/EtOAc 1:1 to 1:2) to afford the desired L-(−)-lactic acid esters (2.02 g, 75% ; r. 3:4:20:1) as a transparent oil.

Results

Using NMR spectroscopy it was determined that the LaKe esters were produced as outlined above (data not shown)

Conclusion

L-(−)-lactic acid esters 3 and 4 (LaKe esters) can be produced via chemoenzymatic synthesis. This provides an alternative method of preparation of the compounds which furthermore is shorter and more resource friendly.

Example 12

Chemoenzymatic Synthesis of L-(−)-lactic Acid Esters 7 and 8 (DiLa Esters):

Aim of Study

To provide a Chemoenzymatic synthesis of L-(−)-lactic acid esters 7 and 8 (DiLa esters).

Materials and Methods

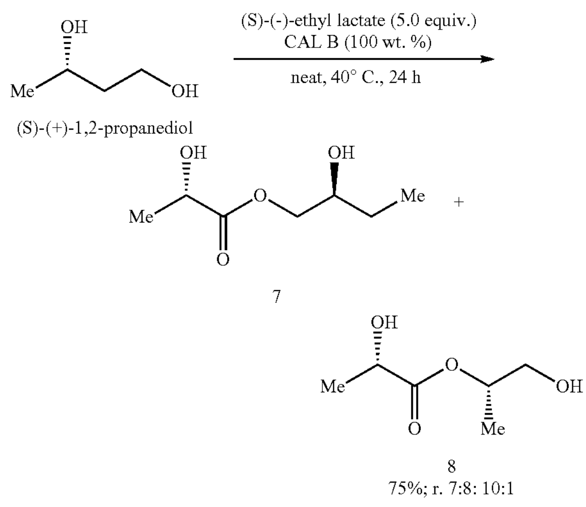

The protocol for the enzymatic synthesis of L-(−)-lactic acid esters 7 and 8 is as follows:

(S)-(+)-1,2-Propanediol (16.0 g, 0.21 mmol, 1.0 equiv.), (S)-(−)-ethyl lactate (124 g, 1.05 mmol, 5.0 equiv.) and Cal B 3 (16.0 g, 100 wt. %) (Lipase B Candida antarctica immobilized on Immobead 150, recombinant from yeast (≈4000 U/g), SIGMA) was placed in a 250 mL flask and heated to 40° C. The mixture was kept at this temperature and stirred carefully (300-350 rpm) for 24 h. The mixture was cooled to rT and filtered under vacuum to remove enzyme beats and the filtrate was concentrated in vacuo. The crude product was subjected to FCC (pentane/EtOAc 1:1 to 1:2) to afford the desired L-(−)-lactic acid esters (16.1 g, 51% ; r. 7:8:10:1) as a transparent oil.

Results

Using NMR spectroscopy it was determined that the DiLa esters were produced as outlined above (data not shown)

Conclusion

L-(−)-lactic acid esters 7 and 8 (DiLa esters) can be produced via Chemoenzymatic synthesis. This provides an alternative method of preparation of the compounds which furthermore is shorter and more resource friendly.

Without being bound by theory, the data presented in examples 11 and 12 can also be performed for the synthesis of KeLa esters, starting from ethyl (R)-(−)-3-hydroxy butyrate and (S)-(+)-1,2-propanediol.

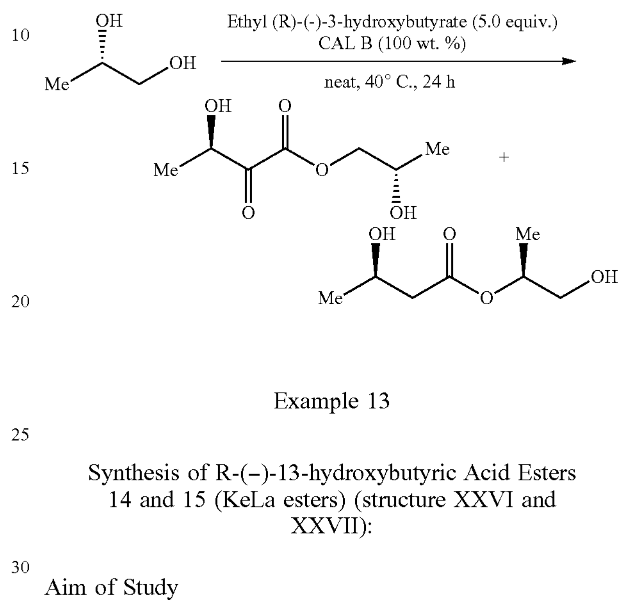

Example 13

Synthesis of R-(−)-13-hydroxybutyric Acid Esters 14 and 15 (KeLa esters) (structure XXVI and XXVII):

Aim of Study

Synthesis of R-(−)-3-hydroxybutyric Acid Esters 12 and 13 (KeLa Esters):

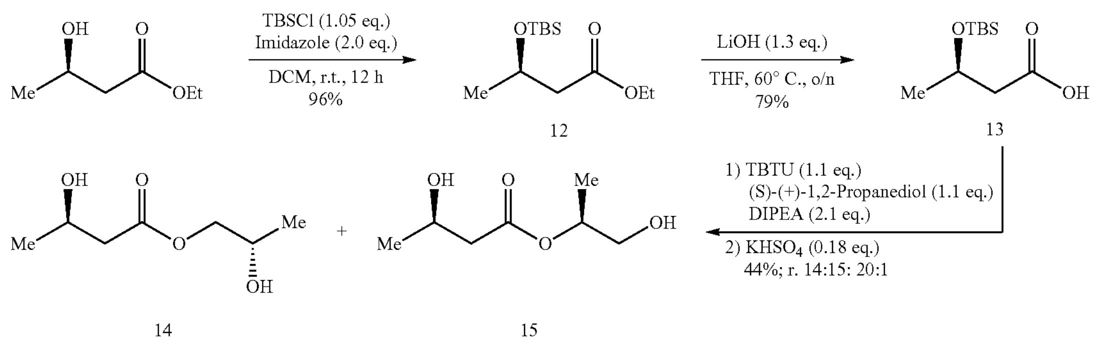

Ethyl (R)-3-((tert-butyldimethylsilyl)oxy)butanoate (12):

12

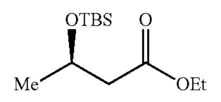

To a solution of ethyl (R)-(−)-3-hydroxybutyrate (50.0 g, 378 mmol, 1.0 eq.) in anhydrous DCM (500 mL) was added TBSCI (59.8 g, 397 mmol, 1.05 eq.) followed by imidazole (51.5 g, 756 mmol, 2.0 eq.). The mixture was stirred at r.t. for 12 hours before diluted with sat. aq. NaCl and extracted with EtOAc. The organic 15 layers were combined and washed with 5% aq. HCl and sat. aq. NaCl. The organic layer was then dried over $Na_2SO_4$, filtered and concentrated to afford ethyl (R)-3-(tert-butyldimethylsilyloxy)butanoate (89.0 g, 96%)

$R_f$ 0.65 (Pentane/$Et_2O$ 95:5, $KMnO_4$).

$^1$H NMR (400 MHz, $CDCl_3$) $\delta_H$ 4.31-4.21 (m, 1H), 4.18-4.04 (m, 2H), 3.93-3.84 (m, 1H), 2.50-2.41 (m, 1H), 2.39-2.30 (m, 1H), 1.28-1.22 (t, J=7.3 Hz, 3H), 1.21-1.16 (d, J=6.22 Hz, 3H), 0.87-0.83 (s, 9H), 0.06-0.02 (d, J=8.4 Hz, 6H).

$^{13}$C NMR (101 MHz, $CDCl_3$) $\delta_C$ 171.8, 66.0, 60.4, 45.1, 25.1, 24.1, 18.1, −4.4, −4.9.

IR (Neat)

$u_{max}$/cm$^{-1}$ 2957, 2930, 2857, 1738, 1473, 1376, 1300, 1255, 1183, 1139, 1082.

HRMS $[M+Na]^+$=269.1543; found: 269.1545.

$[\alpha]^{24.0}_D$

−24.0° (C=10 mg/mL, $CHCl_3$).

(R)-3-((tert-butyldimethylsilyl)oxy)butanoic acid:

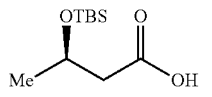

13

To a solution of the (R)-3-((tert-butyldimethylsilyl)oxy) butanoate (89.0 g, 361 mmol, 1.0 eq.) in THF (500 mL) at 0° C. was added a cooled aq. LiOH solution (469 mL, 1 M). The reaction mixture was stirred at 60° C. o/n before concentrated to half of the original volume and extracted with $Et_2O$. The organic extracts were combined before extracted with a sat. aq. $NaHCO_3$ solution. The aqueous layers were combined and acidified with a 1 M aq. $KHSO_4$ solution to reach pH≈3-4. Afterwards, the aqueous solution was extracted thourghly with $Et_2O$ and the organic layers were combined, dried over $Na_2SO_4$ and concentrated to afford (R)-3-((tert-butyldimethylsilyl)oxy)butanoic acid (62.0 g, 79%) as an oil.

$R_f$

4:1, $KMnO_4$).

$^1$H NMR (400 MHz, $CDCl_3$) $\delta_H$ 4.32-4.23 (m, 1H), 2.53-2.38 (m, 2H), 1.24-1.18 (d, J=6.2 Hz 3H), 0.88-0.84 (s, 9H), 0.08-0.04 (d, J=6.9 Hz, 6H.

$^{13}$C NMR (101 MHz, $CDCl_3$) $\delta_C$ 177.9, 65.8, 44.6, 25.8, 23.9, 18.1, −4.4, −5.0.

IR (Neat)

$u_{max}$/cm$^{-1}$ 3675, 2958, 2929, 2900, 2859, 1710, 1408, 1379, 1305, 1253, 1207, 1133, 1080.

HRMS $[M]^-$=217.1265; found: 217.1262.

$[\alpha]^{24.3}_D$

−16.5° (C=35 mg/mL, CHC13).

(S)-2-Hydroxypropyl (R)-3-hydroxybutanoate (14) and (S)-1-hydroxypropan-2-yl (R)-3-hydroxybutanoate (15):

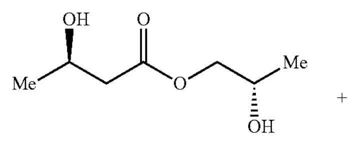

+

14

-continued

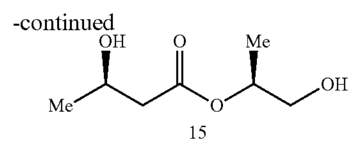

15

The acid (62 g, 284 mmol, 1.0 eq.), TBTU (101 g, 312 mmol, 1.1 eq.) and DIPEA (104 mL, 596 mmol, 2.1 eq.) was dissolved in anhydrous DMF (700 mL) and the mixture was stirred at r.t. for 1 hour. (S)-(+)-1,2-propanediol (23.5 mL, 312 mmol, 1.1 eq.) in anhydrous DMF (30 mL) was then added and the reaction mixture was stirred o/n. at ambient temperature. The reaction mixture was diluted with $CH_2Cl_2$ and the resulting mixture was washed with 1 M aq. HCl, aq. $NaHCO_3$ and water sequentially. The organic layers were then combined, dried over $Na_2SO_4$, filtered and concentrated to afford the crude product. The crude TBS-ether was dissolved in THF:$H_2O$:MeOH (2.5:2.5:1, 500 mL) was added $KHSO_4$ (7.14 g, 52.5 mmol, 0.18 eq.) and the mixture was stirred at r.t. o/n. MeOH was removed under reduced pressure and water was added before the aqueous layer was washed with $Et_2O$. Afterwards, the aqueous phase was extracted thourghly with EtOAc (20x). The organic layers were collected and dried over $Na_2SO_4$, filtered and concentrated. The crude product was purified with FCC (Pentane/EtOAc=1:1 to 1:2) to afford the desired products (19.7 g, 44%; r. 14:15:20:1).

$R_f$ (Pentane/EtOAc 1:4, CAM).

$^1$H NMR

14: (400 MHz, $CDCl_3$) $\delta_H$ 4.25-4.14 (m, 1H), 4.13-4.07 (dd, J=10.7 Hz, 2.6 Hz, 1H), 4.05-3.97 (m, 1H), 3.97-3.90 (dd, J=10.7 Hz, 7.5 Hz, 1H), 3.57-4.34 (s, 1H), 3.23-3.11 (s, 1H), 2.53-2.38 (m, 2H), 1.24-1.20 (d, J=6.3 Hz, 3H), 1.19-1.15 (d, J=6.3 Hz, 3H). 13 C NMR 14: (101 MHz, $CDCl_3$) $\delta_C$ 172.7, 69.7, 65.8, 64.6, 43.3, 22.8, 19.1.

IR (Neat)

$u_{max}$/cm$^{-1}$ 3368, 2974, 2934, 1716, 1377, 1291, 1178, 1123, 1072.

HRMS $[M+Na]^+$=185.0784; found: 185.0788.

$[\alpha]^{24.3}_D$

−17.4° (C=35 mg/mL, $CHCl_3$).

REFERENCES

1—Sun, S. Li, H., Chen, J., Qian, Q. Lactic Acid: No Longer an Inert and End-Product of Glycolysis. Physiology, 2017, 32, 453-463. doi: 10.1152/physio1.00016.2017.

2—Puchalska, P., Crawford, P. A. Multi-dimensional Roles of Ketone Bodies in Fuel Metabolism, Signaling, and Therapeutics. Cell Metab. 2017 25, 262-284. doi: .1016/j.cmet.2016.12.022.

3—Nielsen, R., Møller, N., Gormsen, L, C., Tolbod, L. P., Hansson, N. H., Sorensen, J., Harms, H. J., Frøkiær, J., Eiskjaer, H., Jespersen, N. R., Mellemkjaer, S., Lassen, T. R., Pryds, K., Bøtker, H. E., Wiggers, H. Cardiovascular Effects of Treatment With the Ketone Body 3-Hydroxybutyrate in Chronic Heart Failure Patients. Circulation. 2019, 139, 2129-2141. doi:10.1161/CIRCULATIONAHA.118.036459.

4—Thomsen, H. H., Rittig, N., Johannsen, M., Møller, A. B., Jørgensen, J. O, Jessen, N., Møller, N. Effects of 3-hydroxybutyrate and free fatty acids on muscle protein kinetics and signaling during LPS-induced inflammation in humans: anticatabolic impact of ketone bodies. Am. J. Clin. Nutr. 2018, 108, 857-867. doi: 10.1093/ajcn/nqy170

5—Lauritsen, K. M., Søndergaard, E., Svart, M., Møller, N., Gormsen, L. C. Ketone Body Infusion Increases Circulating Erythropoietin and Bone Marrow Glucose Uptake. Diabetes Care. 2018, 41, e152-e154. doi: 10.2337/dc18-1421.

6—M. C. Petersen, G. I. Shulman, Mechanisms of Insulin Action and Insulin Resistance. Physiol Rev. 98, 2133-2223 (2018).

7—Lambert K. Sørensen, Nikolaj F. Rittig, Emil F. Holmquist, Karl Anker Jorgensen, Jens Otto Lunde Jørgensen, Niels Møller, Mogens Johannsen, Simultaneous determination of β-hydroxybutyrate and β-hydroxy-β-methylbutyrate in human whole blood using hydrophilic interaction liquid chromatography electrospray tandem mass spectrometry, Clinical Biochemistry, Volume 46, Issue 18, 2013, Pages 1877-1883.

8—Rabinowitz & Sven Enerbäck. Lactate: the ugly duckling of energy metabolism. Nature Metabolism volume 2, pages566-571 (2020).

9—Brooks, G. A., Arevalo, J. A., Osmond, A. D., Leija, R. G., Curl, C. C. and Tovar., A. P. Lactate in contemporary biology: A phoenix risen. *J. Physiol.* 1-23 (2021).

Items

1. A compound of the formula I:

(I)

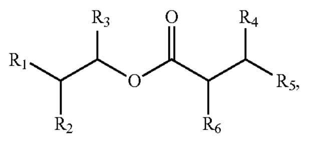

or a pharmaceutical acceptable salt thereof, wherein $R_1$ is $CH_3$, OH, $CH_2OH$ or $CH(CH_3)OH$, $R_2$ is H or OH, $R_3$ is H or $CH_3$, $R_4$ and $R_5$ are H, OH or $CH_3$, and $R_6$ is H or OH.

2. A compound according to item 1, wherein $R_4$ and $R_5$ are H and $R_6$ is OH.

3. A compound according to item 1 or 2, wherein $R_1$ is $CH(CH_3)OH$.

4. A compound according to anyone of item 1-3, wherein $R_2$ is H.

5. A compound according to anyone of item 1-4, wherein $R_3$ is H.

6. A compound according to item 1 or 2 , wherein $R_1$ is $CH_2OH$.

7. A compound according to item 1-2 or 6, wherein $R_2$ is H.

8. A compound according to item 1-2 or anyone of items 6-7, wherein $R_3$ is $CH_3$.

9. A compound according to item 1 or 2, wherein $R_1$ is $CH_3$.

10. A compound according to item 1-2 or 9, wherein $R_2$ is OH.

11. A compound according to item 1 or 2 or anyone of the items 9-10, wherein $R_3$ is H.

12. A compound according to item 1 or 2, wherein $R_1$ is OH.

13. A compound according to item 1-2 or 12, wherein $R_2$ is H.

14. A compound according to item 1-2 or anyone of the items 12-13, wherein $R_3$ is $CH_3$.

15. The compound according to anyone of items 1-14 with stereochemistry according to formula II, (II)

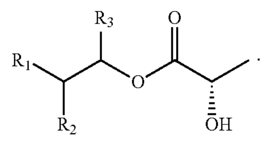

16. The compound according to anyone of items 1-14, with stereochemistry according to formula III, (III)

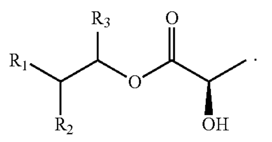

17. The compound according to anyone of items 1-16, with stereochemistry according to formula IV, wherein $R_1$ and $R_2$ is not H, (IV)

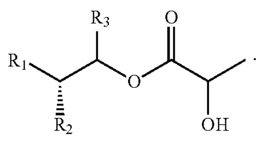

18. The compound according to anyone of items 1-16, with stereochemistry according to formula V, wherein $R_1$ and $R_2$ is not H, (V)

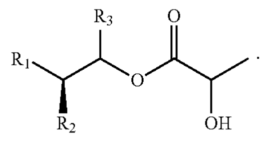

19. The compound according to anyone of items 1-18, with stereochemistry according to formula VI, wherein $R_3$ is $CH_3$, (VI)

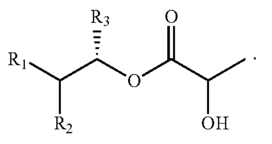

20. compound according to anyone of items 1-18, with stereochemistry according to formula VII, wherein $R_3$ is $CH_3$, (VII)

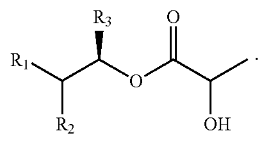

21. The compound according to anyone of items 1-20, wherein $R_1$ is not $CH_3$, OH or $CH_2OH$ and has the stereochemistry according to formula VIII, (VIII)

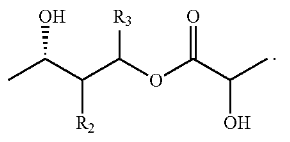

22. The compound according to anyone of items 1-20, wherein $R_1$ is not $CH_3$, OH or $CH_2OH$ and has the stereochemistry according to formula IX, (IX)

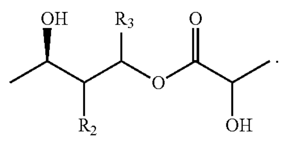

23. The compound according to item 1 with the formula X, (X)

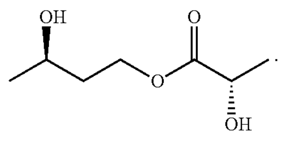

24. The compound according to item 1 with the formula XI, (XI)

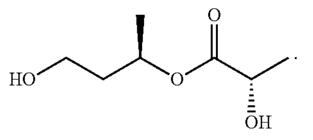

25. The compound according to item 1 with the formula XII, (XII)

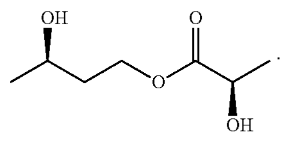

26. The compound according to item 1 with the formula XIII, (XIII)

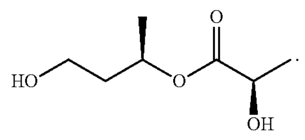

27. The compound according to item 1 with the formula XIV, (XIV)

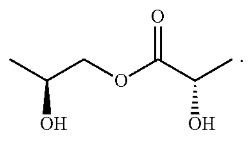

28. The compound according to item 1 with the formula XV, (XV)

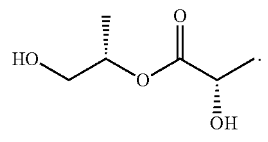

29. The compound according to item 1 with the formula XXVI, (XXVI)

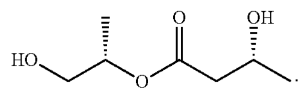

30. The compound according to item 1 with the formula XXVII, (XXVII)

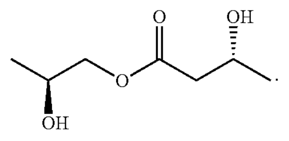

31. A pharmaceutical composition comprising one or more compounds according to items 1-30.

32. The pharmaceutical composition according to item 31 comprising the compounds according to items 23 and 24.
33. The compound according to anyone of the items 1-30 or the pharmaceutical composition according to item 31 or 32 for use as a medicament.
34. The compound or pharmaceutical composition for use according to item 33 in the treatment of inflammatory disease, cancer, epileptic seizures, acute heart failure, Resuscitation, acidosis, traumatic brain injury, acute pancreatitis, hepatitis, myocardial infarction, burns, sepsis, dengue, cognition, sarcopenia, atherosclerosis, neurodegeneration, oxidative stress and wound healing.
35. The compound or pharmaceutical composition for use according to item 33 or 34, wherein the compound is administered to the subject by oral administration.
36. The compound or pharmaceutical composition for use according to item 35, wherein the subject is selected from the group consisting of humans of all ages, other primates (e.g., cynomolgus monkeys, rhesus monkeys); mammals in general, including commercially relevant mammals, such as cattle, pigs, horses, sheep, goats, mink, ferrets, hamsters, cats and dogs, as well as birds.
37. The compound or pharmaceutical composition for use according to item 36, wherein the subject is a human.

The invention claimed is:

1. A food ingredient or food product comprising a compound of formula XXVIII:

(XXVIII)

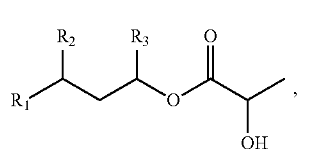

wherein $R_1$, $R_2$ and $R_3$ are $CH_3$, OH and H respectively or $R_1$, $R_2$ and $R_3$ are OH, H and $CH_3$ respectively.

2. The food ingredient or food product according to claim 1, wherein the food ingredient or food product is selected from the group consisting of a nutraceutical, a food supplement, a dietary supplement, a feed, bar, sugar bar, protein bar, powder, gel, beverage, drink, yoghurt, chewing gum, dairy product, sports drink, confectionary product, ice cream, capsule, tablet, sachet, and pouch.

3. A process for producing a compound of formula XXVIII:

(XXVIII)

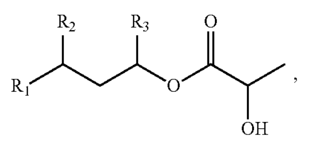

wherein $R_1$, $R_2$ and $R_3$ are $CH_3$, OH and H respectively or $R_1$, $R_2$ and $R_3$ are OH, H and $CH_3$ respectively, the process comprising:

a) providing a compound of formula XLI;

(XLI)

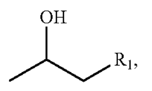

wherein $R_1$ is $CH_2OH$;

b) reacting said compound from step a) with ethyl lactate or ethyl 3-hydroxybutyrate, in the presence of a Lipase; and providing a compound of formula XXVIII:

(XXVIII)

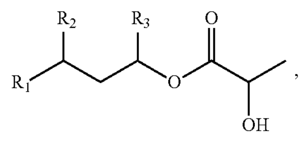

c) wherein $R_1$, $R_2$ and $R_3$ are $CH_3$, OH and H respectively or $R_1$, $R_2$ and $R_3$ are OH, H and $CH_3$ respectively.

4. The process according to claim 3, for producing the compounds X and XI the process comprising:

a) providing a compound of formula XLII;

(XLII)

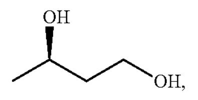

b) reacting said compound from step a) with ethyl lactate, in the presence of a Lipase; and c) providing a compound according to formula X-XI, wherein the compounds X and XI are according to formula (X)

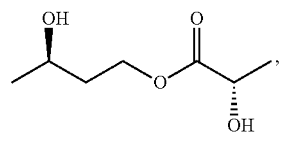

and according to formula XI (XI)

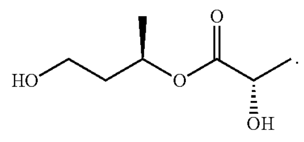

5. The process according to claim 3, wherein said process further comprises a step d) of purifying the provided compounds.

6. The process according to claim 3, wherein said Lipase is immobilized on a solid support.

7. The process according to claim 3, wherein said Lipase is selected from the group consisting of Lipase B, Lipase B *Candida Antarctica* immobilized on Immobead 150, Novozym® 435, CALB, CALB lipase immobilised on an hydrophobic carrier, Lipozyme TL IM and Lipozyme® RM, 1,3 specific lipase.

8. The food ingredient or food product according to claim 1, wherein the food ingredient or food product comprises a compound of the formula XXXII:

(XXXII)

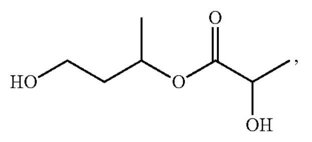

or a compound of the formula XXXI:

(XXXI)

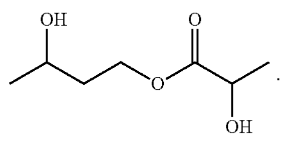

9. The food ingredient or food product according to claim 1, wherein the food ingredient or food product comprises a compound with the stereochemistry according to formula XI;

(XI)

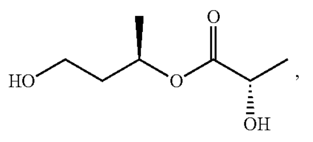

or a compound with the stereochemistry according to formula XIII:

(XIII)

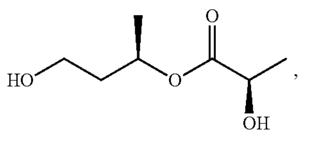

or a compound with the stereochemistry according to formula XVII:

(XVII)

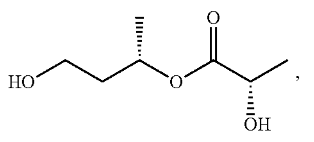

or a compound with the stereochemistry according to formula XIX:

(XIX)

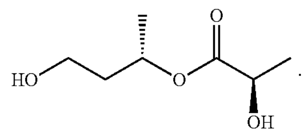

or a compound with the stereochemistry according to formula X:

(X)

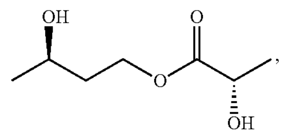

or a compound with the stereochemistry according to formula XII:

(XII)

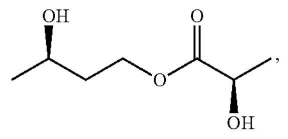

or a compound with the stereochemistry according to formula XVI:

(XVI)

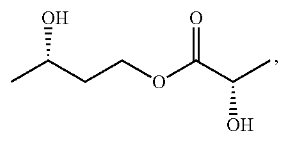

or a compound with the stereochemistry according to formula XVIII:

(XVIII)

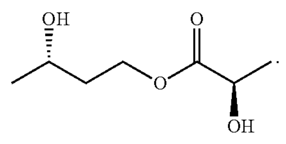

10. The food ingredient or food product according to claim 1, wherein the food ingredient or food product comprises a compound of the formula XXXII:

(XXXII)

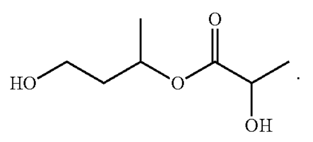

11. The food ingredient or food product according to claim 1, wherein the food ingredient or food product comprises a compound with the stereochemistry according to formula XI:

(XI)

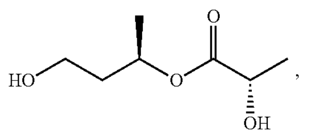

or a compound with the stereochemistry according to formula XIII:

(XIII)

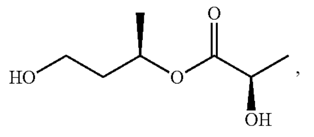

or a compound with the stereochemistry according to formula XVII:

(XVII)

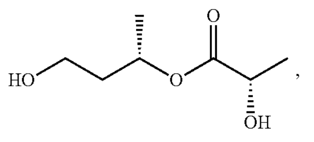

or a compound with the stereochemistry according to formula XIX:

(XIX)

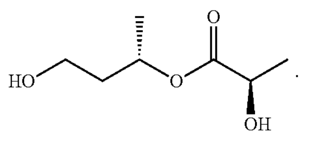

12. The food ingredient or food product according to claim 1, wherein the food ingredient or food product comprises a compound of the XXXI:

(XXXI)

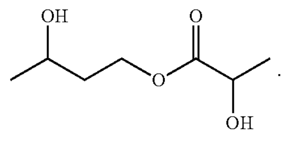

13. The food ingredient or food product according to claim 1, wherein the food ingredient or food product comprises a compound with the stereochemistry according to formula X:

(X)

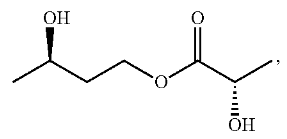

or a compound with the stereochemistry according to formula XII:

(XII)

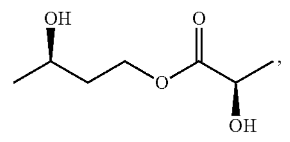

or a compound with the stereochemistry according to formula XVI:

(XVI)

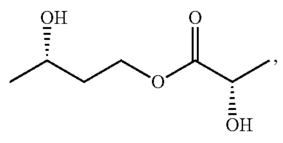

or a compound with the stereochemistry according to formula XVIII:

(XVIII)

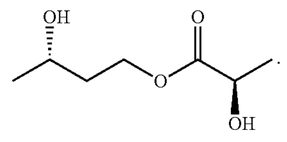

14. The food ingredient or food product according to claim 1, wherein the food ingredient or food product comprises a compound with the stereochemistry according to formula X:

(X)

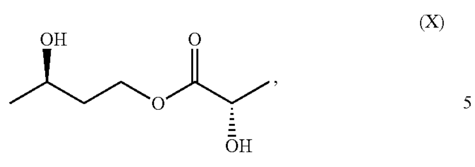

and a compound with the stereochemistry according to formula XI (XI)

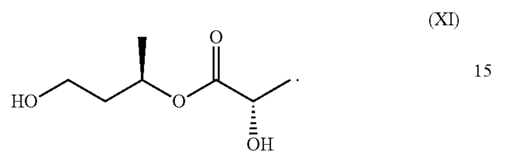

15. The food ingredient or food product according to claim 1, wherein the food ingredient or food product comprises 1,3-butanediol.

16. The food ingredient or food product according to claim 1, wherein the food ingredient or food product comprises a dietetically and/or pharmaceutically acceptable carrier.

* * * * *